(12) United States Patent
Wanker et al.

(10) Patent No.: US 7,078,191 B1
(45) Date of Patent: Jul. 18, 2006

(54) COMPOSITION AND METHOD FOR THE DETECTION OF DISEASES ASSOCIATED WITH AMYLOID-LIKE FIBRIL OR PROTEIN AGGREGATE FORMATION

(75) Inventors: Erich Wanker, Berlin (DE); Hans Lehrach, Berlin (DE); Eberhard Scherzinger, Berlin (DE); Gillian Bates, London (GB)

(73) Assignee: Max-Planck-Gesellschaft zur Förderung Der Wissenschaften E.V., Berlin (DE)

( * ) Notice: Subject to any disclaimer, the term of this patent is extended or adjusted under 35 U.S.C. 154(b) by 0 days.

(21) Appl. No.: 09/463,874

(22) PCT Filed: Jul. 31, 1998

(86) PCT No.: PCT/EP98/04811

§ 371 (c)(1),
(2), (4) Date: Jun. 7, 2000

(87) PCT Pub. No.: WO99/06545

PCT Pub. Date: Feb. 11, 1999

(30) Foreign Application Priority Data

Aug. 1, 1997 (EP) ................................. 97113306

(51) Int. Cl.
C12P 21/04 (2006.01)
C12N 15/00 (2006.01)
C12N 1/20 (2006.01)
A01N 63/00 (2006.01)

(52) U.S. Cl. ................. 435/69.7; 435/69.1; 435/320.1; 435/252.3; 435/252.33; 435/252.8; 435/254.1; 435/254.2; 435/255.1; 435/255.5; 424/93.2; 424/93.21; 424/93.4; 424/93.5; 424/93.51; 424/192.1; 424/193.1; 424/194.1

(58) Field of Classification Search ............... 435/69.1, 435/320.1; 530/350; 536/23.1, 23.5, 23.4
See application file for complete search history.

(56) References Cited

U.S. PATENT DOCUMENTS 5,234,814 A   8/1993  Card et al. ................. 435/7.21
5,593,846 A * 1/1997  Schenk et al. ............... 435/7.9
5,723,301 A   3/1998  Burke et al. .................. 435/7.1
5,795,963 A * 8/1998  Mullan ....................... 530/350

FOREIGN PATENT DOCUMENTS

EP     0 206302 A2   12/1986
EP     0 293 249 A1  11/1988
EP     0 854 364 A1   7/1998
WO     WO95/29243    11/1995
WO     WO96/12544     5/1996
WO     WO96/28471     9/1996
WO     WO97/17445     5/1997

OTHER PUBLICATIONS

Onodera et al., FEBS Letters, 1996, 399, pp. 135-139.*
Evin et al., 1994, Int. J. Exp. Clin Invest., 1, p. 263-280.*
Kisilevsky et al., "Arresting amyloidosis in vivo using small-module anionic sulphonates or sulphates: Implications for Alzheimer's disease", (Feb. 1995), pp. 143-148, *Nature Medicine*, vol. 1, No. 2.
Trottler et al., "Polyglutamine expansion as a pathological epitope in Huntington's disease and four dominant Cerebellar ataxias", (Nov. 23, 1985), pp. 403-406, *Nature* vol. 378.
Gutekunst et al., "Identification and localization of huntingtin in brain and human lymphoblastoid cell lines with anti-fusion protein antibodies", (Sep. 1995), pp. 8710-8714, *Pro. Natl. Acad. Sci. USA* vol. 92 Neurobiology.
M.F. Perutz, "Glutamine repeats and inherited neurodegenerative diseases: molecular aspects", (1996) pp. 848-858, *MRC Laboratory of Molecular Biology*.
Mangiarini et al., "Exon 1 of the HD gene with an expanded CAG repeat is sufficient to cause a progressive neurological phenotype in transgenic mice", (Nov. 1, 1996), pp. 493-506, *Cell*, vol. 87.
Stott et al., "Incorporation of glutamine repeats makes protein oligomerize: implications for neurodegenerative Diseases", (Jul. 1995), pp. 6509-6513, *Pro. Natl. Acad. Sci. USA*, vol. 92, Biochemistry.

(Continued)

*Primary Examiner*—Olga N. Chernyshev
(74) *Attorney, Agent, or Firm*—Wolf, Greenfield & Sacks, P.C.

(57) ABSTRACT

The present invention relates to novel compositions useful for elucidating the onset or progress of diseases such as Huntington's disease, that are associated with the formation of fibrils or protein aggregates. Further, the present invention relates to methods for monitoring formation of fibrils or protein aggregates as well as to methods for identifying inhibitors of fibril or protein aggregate formation. Additionally, the invention relates to inhibitors of the formation of fibrils or protein aggregates identified by the method of the invention as well as to pharmaceutical compositions that include the inhibitors.

13 Claims, 12 Drawing Sheets

OTHER PUBLICATIONS

Figure 1:
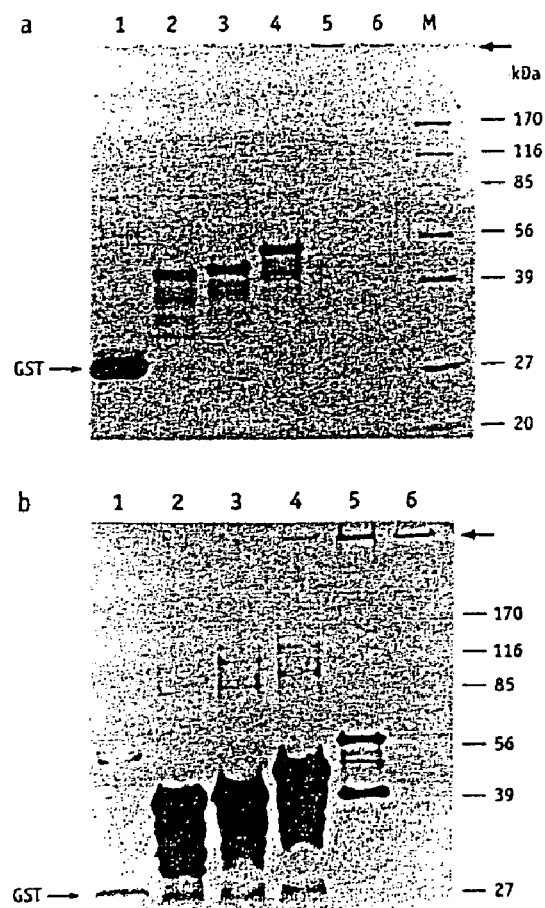

Merlini et al., "Interaction of the anthracycline 4'-iodo-4'-deoxydoxorubicin with amyloid fibrils: Inhibition of amyloidogenesis", (Mar. 1995), pp. 2959-2963, *Proc. Natl. Acad. Sci. USA*, vol. 92, Medical Sciences.

Scherzinger, et al., "Huntingtin-encoded polyglutamine expansions form amyloid-like protein aggregates in vitro and in vivo", (Aug. 8, 1997), pp. 549-558, *Cell*, vol. 90.

Davies et al., "Formation of neuronal intranuclear inclusions underlies the neurological dysfunction in mice Transgenic for the HD mutation", (Aug. 8, 1997), pp. 537-548, *Cell*, vol. 90.

Derwent, "Nucleic acid fragments associated with spinocerebellar ataxis type 2-contain increased number of CAG repeat region compared to normal gene", (May 7, 1998), XP-002101183.

Tateishe et al., "Removal of causative agent of creutzefeldt-jakob disease (CJD) through membrane filtration method", (1993), pp. 357-362, *Membrane*, 18(6).

The Huntington's Disease Collaborative Research Group, "A Novel Gene Containing a Trinucleotide Repeat That is Expanded and Unstable on Huntington's Disease Chromosomes", Cell, Mar. 26, 1993, vol. 72, 971-983.

Bates, G.P. et al., Transgenic models of Huntington's disease. Hum Mol Genet. 1997;6(10):1633-7.

Becher, M.W. et al., Intranuclear neuronal inclusions in Huntington's disease and dentatorubral and pallidoluysian atrophy: correlation between the density of inclusions and ITI5 CAG triplet repeat length. Neurobiol Dis. Apr. 1998;4(6):387-97.

Beyreuther, K. et al., Alzheimer's disease. Tangle disentanglement. Nature. Oct. 10, 1996;383(6600):476-7.

Booth, D.R. et al., Instability, unfolding and aggregation of human lysozyme variants underlying amyloid fibrillogenesis. Nature. Feb. 27, 1997;385(6619):787-93.

Burke, J.R. et al., Huntingtin and DRPLA proteins selectively interact with the enzyme GAPDH. Nat Med. Mar. 1996;2(3):347-50.

Caputo, C.B. et al., Amyloid-like properties of a synthetic peptide corresponding to the carboxy terminus of beta-amyloid protein precursor. Arch Biochem Biophys. Jan. 1992;292(1):199-205.

Caughey, B. and Chesebro, B. Prion protein and the transmissible spongiform encephalopaties. Trends Cell Biol. 1997; 7: 56-62.

De Rooij, K.E. et al., Subcellular localization of the Huntington's disease gene product in cell lines by immunofluorescence and biochemical subcellular fractionation. Hum Mol Genet. Aug. 1996;5(8):1093-9.

Difiglia, M. et al., Aggregation of huntingtin in neuronal intranuclear inclusions and dystrophic neurites in brain. Science. Sep. 26, 1997;277(5334):1990-3.

Difiglia, M. et al., Huntingtin is a cytoplasmic protein associated with vesicles in human and rat brain neurons. Neuron. May 1995;14(5):1075-81.

Duyao, M.P. et al., Inactivation of the mouse Huntington's disease gene homolog Hdh. Science. Jul. 21, 1995;269(5222):407-10.

Georgalis, Y. et al., Huntingtin aggregation monitored by dynamic light scattering. Proc Natl Acad Sci U S A. May 26, 1998;95(11):6118-21.

Glenner, G.G. Amyloid deposits and amyloidosis. The beta-fibrilloses (first of two parts). N Engl J Med. Jun. 5, 1980;302(23):1283-92 and 1333-1343.

Goldberg, Y.P. et al., Cleavage of huntingtin by apopain, a proapoptotic cysteine protease, is modulated by the polyglutamine tract. Nat Genet. Aug. 1996;13(4):442-9.

HDCRG. A novel gene containing a trinucleotide repeat that is expanded and unstable on Huntington's disease chromosomes. The Huntington'Disease Collaborative Research Group. Cell. Mar. 26, 1993;72(6):971-83.

Holmberg, M. et al., Spinocerebellar ataxia type 7 (SCA7): a neurodegenerative disorder with neuronal intranuclear inclusions. Hum Mol Genet. May 1998;7(5):913-8.

Hoogeveen, A.T. et al., Characterization and localization of the Huntington disease gene product. Hum Mol Genet. Dec. 1993;2(12):2069-73.

Igarashi, S. et al., Suppression of aggregate formation and apoptosis by transglutaminase inhibitors in cells expressing truncated DRPLA protein with an expanded polyglutamine stretch. Nat Genet. Feb. 1998;18(20:111-7.

Ikeda, H. et al., Expanded polyglutamine in the Machado-Joseph disease protein induces cell death in vitro and in vivo. Nat Genet. Jun. 1996;13(2):196-202.

Jarrett, J.T. and Lansbury, P.T. Seeding "one-dimensional crystallization" of amyloid: a pathogenic mechanism in Alzheimer's disease and scrapie? Cell. Jun. 18, 1993;73(6):1055-8.

Kalchman, M.A. et al., HIP1, a human homologue of S. cerevisiae Sla2p, interacts with membrane-associated huntingtin in the brain. Nat Genet. May 1997;16(1):44-53.

Kalchman, M.A. et al., Huntingtin is ubiquitinated and interacts with a specific ubiquitin-conjugating enzyme. J Biol Chem. Aug. 9, 1996;271(32):19385-94.

Li, X.-J. et al., A huntingtin-associated protein enriched in brain with implications for pathology. Nature. Nov. 23, 1995;378(6555):398-402.

Lim, K. et al., Three-dimensional structure of Schistosoma japonicum glutathione S-transferase fused with a six-amino acid conserved neutralizing epitope of gp41 from HIV. Protein Sci. Dec. 1994;3(12):2233-44.

Matilla, A. et al., The cerebellar leucine-rich acidic nuclear protein interacts with ataxin-1. Nature. Oct. 30, 1997.389(6654):974-8. Erratum in: Nature Feb. 19, 1998;391(6669):818.

Onodera, O. et al., Toxicity of expanded polyglutamine-domain proteins in *Escherichia coli*. FEBS Lett. Dec. 9, 1996;399(1-2):135-9.

Paulson, H.L. et al., Intranuclear inclusions of expanded polyglutamine protein in spinocerebellar ataxia type 3. Neuron. Aug. 1997;19(2):333-44.

Perutz, M.F. et al., Glutamine repeats as polar zippers: their possible role in inherited neurodegenerative diseases. Proc Natl Acad Sci U S A. Jun. 7, 1994;91(12):5355-8.

Portera-Cailliau, C. et al., Evidence for apoptotic cell death in Huntington disease and excitotoxic animal models. J Neurosci. May 1995;15(5 Pt 2):3775-87.

Prusiner, S.B. et al., Scrapie prions aggregate to form amyloid-like birefringent rods. Cell. Dec. 1983;35(2 Pt 1):349-58.

Roizin, L. et al., Neuronal nuclear-cytoplasmic changer in Huntington's chorea. J. Neurol. Sci. 1983; 61: 37-47.

Roos, R.A.C. et al., Nuclear membrane indentations in Huntington's chorea. J Neurol Sci. Sep. 1983;61(1):37-47.

Ross, C.A. When more is less: pathogenesis of glutamine repeat neurodegenerative diseases. Neuron. Sep. 1995;15(3):493-6.

Rubinsztein, D.C. et al., Phenotypic characterization of individuals with 30-40 CAG repeats in the Huntington disease (HD) gene reveals HD cases with 36 repeats and apparently normal elderly individuals with 36-39 repeats. Am J Hum Genet. Jul. 1996;59(1):16-22.

Sathasivam, K. et al., Identification of an HD patient with a (CAG)180 repeat expansion and the propagation of highly expanded CAG repeats in lambda phage. Hum Genet. May 1997;99(5):692-5.

Schatz, P.J. Use of peptide libraries to map the substrate specificity of a peptide-modifying enxzyme: a 13 residue consensus peptide specifies biotinylation in *Escherichia coli*. Biotechnology (N Y). Oct. 1993;11(10):1138-43.

Scherzinger, E. et al., Huntingtin-encoded polyglutamine expansions form amyloid-like protein aggregates in vitro and in vivo. Cell. Aug. 8, 1997;90(3):549-58.

Sharp, A.H. et al., Widespread expression of Huntington'disease gene (IT15) protein product. Neuron. May 1995;14(5):1065-74.

Sittler, A. et al., Alternative splicing of exon 14 determines nuclear or cytoplasmic localisation of fmr1 protein isoforms. Hum Mol Genet. Jan. 1996;5(1):95-102.

Sittler, A. et al., SH3GL3 associates with the Huntingtin exon 1 protein and promotes the formation of polygln-containing protein aggregates. Mol Cell. Oct. 1998;2(4):427-36.

Skinner, P.J. et al., Ataxin-1 with an expanded glutamine tract alters nuclear matrix-associated structures. Nature. Oct. 30, 1997;389(6654):971-4. Erratum in: Nature Jan. 15, 1998;391(6664):307.

Smith, D.B. et al., Single-step purification of polypeptides expressed in *Escherichia coli* as fusions with glutathione S-transferase. Gene. Jul. 15, 1988;67(1):31-40.

Tellez-Nagel, I. et al., Studies on brain biopsies of patients with Huntington's chorea, J Neuropathol Exp Neurol. Apr. 1974;33(2):308-32.

Towbin, H. et al., Electrophoretic transfer of proteins from polyacrylamide gels to nitrocellulose sheets: procedure and some applications. Proc Natl Acad Sci U S A. Sep. 1979;76(9):4350-4.

Trottier, Y. et al., Cellular localization of the Huntington's disease protein and discrimination of the normal and mutated form. Nat Genet. May, 1995;10(1):104-10.

Vonsattel, J.-P. et al., Neuropathological classification of Huntington's disease. J Neuropathol Exp Neurol. Nov. 1985;44(6):559-77.

Wanker, E.E. et al., HIP-I: a huntingtin interacting protein isolated by the yeast two-hydrid system. Hum Mol Genet. Mar. 1997;6(3):487-95.

* cited by examiner

SEQUENCE LISTING

```
<160> NUMBER OF SEQ ID NOS:  41

<210> SEQ ID NO 1
<211> LENGTH: 38
<212> TYPE: DNA
<213> ORGANISM: Artificial Sequence
<220> FEATURE:
<223> OTHER INFORMATION: Oligonucleotide Primer

<400> SEQUENCE: 1
tgggatccgc atggcgaccc tggaaaagct gatgaagg                      38

<210> SEQ ID NO 2
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 2
ggagtcgact cacggtcggt gcagcggctc ctcagc                        36

<210> SEQ ID NO 3
<211> LENGTH: 39
<212> TYPE: DNA
<213> ORGANISM: Artificial Sequence
<220> FEATURE:
<223> OTHER INFORMATION: Oligonucleotide Primer

<400> SEQUENCE: 3
ctcctcgagc ggcggtggcg gctgttgctg ctgctgctg                     39

<210> SEQ ID NO 4
<211> LENGTH: 51
<212> TYPE: DNA
<213> ORGANISM: Artificial Sequence
<220> FEATURE:
<223> OTHER INFORMATION: Oligonucleotide Primer

<400> SEQUENCE: 4
```

-continued

```
cgctcgaggg tatcttcgag gcccagaaga tcgagtggcg atcaccatga g                    51

<210> SEQ ID NO 5
<211> LENGTH: 54
<212> TYPE: DNA
<213> ORGANISM: Artificial Sequence
<220> FEATURE:
<223> OTHER INFORMATION: Oligonucleotide Primer

<400> SEQUENCE: 5
ggccgctcat ggtgatcgcc actcgatctt ctgggcctcg aagataccct cgag               54

<210> SEQ ID NO 6
<211> LENGTH: 94
<212> TYPE: PRT
<213> ORGANISM: Homo Sapiens

<400> SEQUENCE: 6

Ile Glu Gly Arg Gly Ile Arg Met Ala Thr Leu Glu Lys Leu Met Lys
 1               5                  10                  15

Ala Phe Glu Ser Leu Lys Ser Phe Gln Gln Gln Gln Gln Gln Gln Gln
                20                  25                  30

Gln Gln Gln Gln Gln Gln Gln Gln Gln Gln Gln Pro Pro Pro Pro
            35                  40                  45

Pro Pro Pro Pro Pro Pro Gln Leu Pro Gln Pro Pro Pro Gln Ala
    50                  55                  60

Gln Pro Leu Leu Pro Gln Pro Gln Pro Pro Pro Pro Pro Pro Pro
65                  70                  75                  80

Pro Pro Gly Pro Ala Val Ala Glu Glu Pro Leu His Arg Pro
                85                  90

<210> SEQ ID NO 7
<211> LENGTH: 95
<212> TYPE: PRT
<213> ORGANISM: Homo Sapiens

<400> SEQUENCE: 7

Ile Glu Gly Arg Gly Ile Arg Met Ala Thr Leu Glu Lys Leu Met Lys
 1               5                  10                  15

Ala Phe Glu Ser Leu Lys Ser Phe Gln Gln Gln Gln Gln Gln Gln Gln
                20                  25                  30

Gln Gln Gln Gln Gln Gln Gln Gln Gln Gln Gln Gln Pro Pro Pro
            35                  40                  45

Pro Pro Pro Pro Pro Pro Pro Gln Leu Pro Gln Pro Pro Pro Gln
    50                  55                  60

Ala Gln Pro Leu Leu Pro Gln Pro Gln Pro Pro Pro Pro Pro Pro Pro
65                  70                  75                  80

Pro Pro Pro Gly Pro Ala Val Ala Glu Glu Pro Leu His Arg Pro
                85                  90                  95

<210> SEQ ID NO 8
<211> LENGTH: 96
<212> TYPE: PRT
<213> ORGANISM: Homo Sapiens

<400> SEQUENCE: 8

Ile Glu Gly Arg Gly Ile Arg Met Ala Thr Leu Glu Lys Leu Met Lys
 1               5                  10                  15

Ala Phe Glu Ser Leu Lys Ser Phe Gln Gln Gln Gln Gln Gln Gln Gln
```

-continued

```
                 20                  25                  30

Gln Gln Gln Gln Gln Gln Gln Gln Gln Gln Gln Gln Gln Pro Pro
             35                  40                  45

Pro Pro Pro Pro Pro Pro Pro Pro Pro Gln Leu Pro Gln Pro Pro
         50                  55                  60

Gln Ala Gln Pro Leu Leu Pro Gln Pro Gln Pro Pro Pro Pro Pro
 65                  70                  75                  80

Pro Pro Pro Pro Gly Pro Ala Val Ala Glu Pro Leu His Arg Pro
                 85                  90                  95

<210> SEQ ID NO 9
<211> LENGTH: 97
<212> TYPE: PRT
<213> ORGANISM: Homo Sapiens

<400> SEQUENCE: 9

Ile Glu Gly Arg Gly Ile Arg Met Ala Thr Leu Glu Lys Leu Met Lys
 1               5                  10                  15

Ala Phe Glu Ser Leu Lys Ser Phe Gln Gln Gln Gln Gln Gln Gln
                 20                  25                  30

Gln Gln Gln Gln Gln Gln Gln Gln Gln Gln Gln Gln Gln Gln Pro
             35                  40                  45

Pro Pro Pro Pro Pro Pro Pro Pro Pro Gln Leu Pro Gln Pro Pro
         50                  55                  60

Pro Gln Ala Gln Pro Leu Leu Pro Gln Pro Gln Pro Pro Pro Pro
 65                  70                  75                  80

Pro Pro Pro Pro Pro Gly Pro Ala Val Ala Glu Glu Pro Leu His Arg
                 85                  90                  95

Pro

<210> SEQ ID NO 10
<211> LENGTH: 98
<212> TYPE: PRT
<213> ORGANISM: Homo Sapiens

<400> SEQUENCE: 10

Ile Glu Gly Arg Gly Ile Arg Met Ala Thr Leu Glu Lys Leu Met Lys
 1               5                  10                  15

Ala Phe Glu Ser Leu Lys Ser Phe Gln Gln Gln Gln Gln Gln Gln
                 20                  25                  30

Gln Gln Gln Gln Gln Gln Gln Gln Gln Gln Gln Gln Gln Gln Gln
             35                  40                  45

Pro Pro Pro Pro Pro Pro Pro Pro Pro Pro Gln Leu Pro Gln Pro
         50                  55                  60

Pro Pro Gln Ala Gln Pro Leu Leu Pro Gln Pro Gln Pro Pro Pro
 65                  70                  75                  80

Pro Pro Pro Pro Pro Pro Gly Pro Ala Val Ala Glu Glu Pro Leu His
                 85                  90                  95

Arg Pro

<210> SEQ ID NO 11
<211> LENGTH: 99
<212> TYPE: PRT
<213> ORGANISM: Homo Sapiens

<400> SEQUENCE: 11

Ile Glu Gly Arg Gly Ile Arg Met Ala Thr Leu Glu Lys Leu Met Lys
```

```
                    1               5                  10                 15
            Ala Phe Glu Ser Leu Lys Ser Phe Gln Gln Gln Gln Gln Gln Gln
                            20                  25                  30
            Gln Gln Gln Gln Gln Gln Gln Gln Gln Gln Gln Gln Gln Gln Gln
                    35                  40                  45
            Gln Pro Pro Pro Pro Pro Pro Pro Pro Pro Pro Gln Leu Pro Gln
                50                  55                  60
            Pro Pro Pro Gln Ala Gln Pro Leu Leu Pro Gln Pro Gln Pro Pro
            65                  70                  75                  80
            Pro Pro Pro Pro Pro Pro Gly Pro Ala Val Ala Glu Glu Pro Leu
                            85                  90                  95
            His Arg Pro

<210> SEQ ID NO 12
<211> LENGTH: 100
<212> TYPE: PRT
<213> ORGANISM: Homo Sapiens

<400> SEQUENCE: 12

Ile Glu Gly Arg Gly Ile Arg Met Ala Thr Leu Glu Lys Leu Met Lys
            1               5                   10                  15
            Ala Phe Glu Ser Leu Lys Ser Phe Gln Gln Gln Gln Gln Gln Gln
                            20                  25                  30
            Gln Gln Gln Gln Gln Gln Gln Gln Gln Gln Gln Gln Gln Gln Gln
                    35                  40                  45
            Gln Gln Pro Pro Pro Pro Pro Pro Pro Pro Pro Pro Gln Leu Pro
                50                  55                  60
            Gln Pro Pro Pro Gln Ala Gln Pro Leu Leu Pro Gln Pro Gln Pro Pro
            65                  70                  75                  80
            Pro Pro Pro Pro Pro Pro Pro Gly Pro Ala Val Ala Glu Glu Pro
                            85                  90                  95
            Leu His Arg Pro
                        100

<210> SEQ ID NO 13
<211> LENGTH: 101
<212> TYPE: PRT
<213> ORGANISM: Homo Sapiens

<400> SEQUENCE: 13

Ile Glu Gly Arg Gly Ile Arg Met Ala Thr Leu Glu Lys Leu Met Lys
            1               5                   10                  15
            Ala Phe Glu Ser Leu Lys Ser Phe Gln Gln Gln Gln Gln Gln Gln
                            20                  25                  30
            Gln Gln Gln Gln Gln Gln Gln Gln Gln Gln Gln Gln Gln Gln Gln
                    35                  40                  45
            Gln Gln Gln Pro Pro Pro Pro Pro Pro Pro Pro Pro Pro Gln Leu
                50                  55                  60
            Pro Gln Pro Pro Pro Gln Ala Gln Pro Leu Leu Pro Gln Pro Gln Pro
            65                  70                  75                  80
            Pro Pro Pro Pro Pro Pro Pro Pro Gly Pro Ala Val Ala Glu Glu
                            85                  90                  95
            Pro Leu His Arg Pro
                        100

<210> SEQ ID NO 14
```

```
<211> LENGTH: 102
<212> TYPE: PRT
<213> ORGANISM: Homo Sapiens

<400> SEQUENCE: 14

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
                20                  25                  30

Gln Gln Gln Gln Gln Gln Gln Gln Gln Gln Gln Gln Gln Gln Gln Gln
            35                  40                  45

Gln Gln Gln Gln Pro Pro Pro Pro Pro Pro Pro Pro Pro Pro Pro Gln
        50                  55                  60

Leu Pro Gln Pro Pro Pro Gln Ala Gln Pro Leu Leu Pro Gln Pro Gln
65                  70                  75                  80

Pro Pro Pro Pro Pro Pro Pro Pro Gly Pro Ala Val Ala Glu
                85                  90                  95

Glu Pro Leu His Arg Pro
            100

<210> SEQ ID NO 15
<211> LENGTH: 103
<212> TYPE: PRT
<213> ORGANISM: Homo Sapiens

<400> SEQUENCE: 15

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
                20                  25                  30

Gln Gln Gln Gln Gln Gln Gln Gln Gln Gln Gln Gln Gln Gln Gln Gln
            35                  40                  45

Gln Gln Gln Gln Gln Pro Pro Pro Pro Pro Pro Pro Pro Pro Pro Pro
        50                  55                  60

Gln Leu Pro Gln Pro Pro Pro Gln Ala Gln Pro Leu Leu Pro Gln Pro
65                  70                  75                  80

Gln Pro Pro Pro Pro Pro Pro Pro Pro Pro Gly Pro Ala Val Ala
                85                  90                  95

Glu Glu Pro Leu His Arg Pro
            100

<210> SEQ ID NO 16
<211> LENGTH: 104
<212> TYPE: PRT
<213> ORGANISM: Homo Sapiens

<400> SEQUENCE: 16

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
                20                  25                  30

Gln Gln Gln Gln Gln Gln Gln Gln Gln Gln Gln Gln Gln Gln Gln Gln
            35                  40                  45

Gln Gln Gln Gln Gln Gln Pro Pro Pro Pro Pro Pro Pro Pro Pro Pro
        50                  55                  60

Pro Gln Leu Pro Gln Pro Pro Pro Gln Ala Gln Pro Leu Leu Pro Gln
65                  70                  75                  80
```

```
Pro Gln Pro Pro Pro Pro Pro Pro Pro Pro Gly Pro Ala Val
            85                  90              95

Ala Glu Glu Pro Leu His Arg Pro
            100

<210> SEQ ID NO 17
<211> LENGTH: 105
<212> TYPE: PRT
<213> ORGANISM: Homo Sapiens

<400> SEQUENCE: 17

Ile Glu Gly Arg Gly Ile Arg Met Ala Thr Leu Glu Lys Leu Met Lys
 1               5                  10                  15

Ala Phe Glu Ser Leu Lys Ser Phe Gln Gln Gln Gln Gln Gln Gln
            20                  25                  30

Gln Gln Gln Gln Gln Gln Gln Gln Gln Gln Gln Gln Gln Gln Gln
        35                  40                  45

Gln Gln Gln Gln Gln Gln Pro Pro Pro Pro Pro Pro Pro Pro
    50                  55                  60

Pro Pro Gln Leu Pro Gln Pro Pro Gln Ala Gln Pro Leu Leu Pro
65                  70                  75                  80

Gln Pro Gln Pro Pro Pro Pro Pro Pro Pro Pro Pro Gly Pro Ala
            85                  90                  95

Val Ala Glu Glu Pro Leu His Arg Pro
            100                 105

<210> SEQ ID NO 18
<211> LENGTH: 106
<212> TYPE: PRT
<213> ORGANISM: Homo Sapiens

<400> SEQUENCE: 18

Ile Glu Gly Arg Gly Ile Arg Met Ala Thr Leu Glu Lys Leu Met Lys
 1               5                  10                  15

Ala Phe Glu Ser Leu Lys Ser Phe Gln Gln Gln Gln Gln Gln Gln
            20                  25                  30

Gln Gln Gln Gln Gln Gln Gln Gln Gln Gln Gln Gln Gln Gln Gln
        35                  40                  45

Gln Gln Gln Gln Gln Gln Gln Pro Pro Pro Pro Pro Pro Pro
    50                  55                  60

Pro Pro Pro Gln Leu Pro Gln Pro Pro Gln Ala Gln Pro Leu Leu
65                  70                  75                  80

Pro Gln Pro Gln Pro Pro Pro Pro Pro Pro Pro Pro Pro Gly Pro
            85                  90                  95

Ala Val Ala Glu Glu Pro Leu His Arg Pro
            100                 105

<210> SEQ ID NO 19
<211> LENGTH: 107
<212> TYPE: PRT
<213> ORGANISM: Homo Sapiens

<400> SEQUENCE: 19

Ile Glu Gly Arg Gly Ile Arg Met Ala Thr Leu Glu Lys Leu Met Lys
 1               5                  10                  15

Ala Phe Glu Ser Leu Lys Ser Phe Gln Gln Gln Gln Gln Gln Gln
            20                  25                  30

Gln Gln Gln Gln Gln Gln Gln Gln Gln Gln Gln Gln Gln Gln Gln
```

-continued

```
                  35                  40                  45

Gln Gln Gln Gln Gln Gln Gln Gln Pro Pro Pro Pro Pro Pro
    50                  55                  60

Pro Pro Pro Pro Gln Leu Pro Gln Pro Pro Gln Ala Gln Pro Leu
65                  70                  75                  80

Leu Pro Gln Pro Gln Pro Pro Pro Pro Pro Pro Pro Pro Gly
                85                  90                  95

Pro Ala Val Ala Glu Glu Pro Leu His Arg Pro
            100                 105

<210> SEQ ID NO 20
<211> LENGTH: 108
<212> TYPE: PRT
<213> ORGANISM: Homo Sapiens

<400> SEQUENCE: 20

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln
                20                  25                  30

Gln Gln Gln Gln Gln Gln Gln Gln Gln Gln Gln Gln Gln Gln
            35                  40                  45

Gln Gln Gln Gln Gln Gln Gln Gln Gln Pro Pro Pro Pro Pro
    50                  55                  60

Pro Pro Pro Pro Pro Gln Leu Pro Gln Pro Pro Gln Ala Gln Pro
65                  70                  75                  80

Leu Leu Pro Gln Pro Gln Pro Pro Pro Pro Pro Pro Pro Pro
                85                  90                  95

Gly Pro Ala Val Ala Glu Glu Pro Leu His Arg Pro
            100                 105

<210> SEQ ID NO 21
<211> LENGTH: 109
<212> TYPE: PRT
<213> ORGANISM: Homo Sapiens

<400> SEQUENCE: 21

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln
                20                  25                  30

Gln Gln Gln Gln Gln Gln Gln Gln Gln Gln Gln Gln Gln Gln
            35                  40                  45

Gln Gln Gln Gln Gln Gln Gln Gln Gln Gln Pro Pro Pro Pro
    50                  55                  60

Pro Pro Pro Pro Pro Gln Leu Pro Gln Pro Pro Gln Ala Gln
65                  70                  75                  80

Pro Leu Leu Pro Gln Pro Gln Pro Pro Pro Pro Pro Pro Pro Pro
                85                  90                  95

Pro Gly Pro Ala Val Ala Glu Glu Pro Leu His Arg Pro
            100                 105

<210> SEQ ID NO 22
<211> LENGTH: 110
<212> TYPE: PRT
<213> ORGANISM: Homo Sapiens

<400> SEQUENCE: 22
```

-continued

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Pro Pro Pro
    50                  55                  60

Pro Pro Pro Pro Pro Pro Pro Gln Leu Pro Gln Pro Pro Gln Ala
65                  70                  75                  80

Gln Pro Leu Leu Pro Gln Pro Gln Pro Pro Pro Pro Pro Pro
            85                  90                  95

Pro Pro Gly Pro Ala Val Ala Glu Glu Pro Leu His Arg Pro
        100                 105                 110

<210> SEQ ID NO 23
<211> LENGTH: 111
<212> TYPE: PRT
<213> ORGANISM: Homo Sapiens

<400> SEQUENCE: 23

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Gln Pro Pro Pro
    50                  55                  60

Pro Pro Pro Pro Pro Pro Pro Gln Leu Pro Gln Pro Pro Gln
65                  70                  75                  80

Ala Gln Pro Leu Leu Pro Gln Pro Gln Pro Pro Pro Pro Pro Pro
            85                  90                  95

Pro Pro Pro Gly Pro Ala Val Ala Glu Glu Pro Leu His Arg Pro
        100                 105                 110

<210> SEQ ID NO 24
<211> LENGTH: 112
<212> TYPE: PRT
<213> ORGANISM: Homo Sapiens

<400> SEQUENCE: 24

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Pro Pro
    50                  55                  60

Pro Pro Pro Pro Pro Pro Pro Pro Gln Leu Pro Gln Pro Pro
65                  70                  75                  80

Gln Ala Gln Pro Leu Leu Pro Gln Pro Gln Pro Pro Pro Pro Pro
            85                  90                  95

Pro Pro Pro Pro Gly Pro Ala Val Ala Glu Glu Pro Leu His Arg Pro
        100                 105                 110

<210> SEQ ID NO 25
<211> LENGTH: 113
<212> TYPE: PRT
<213> ORGANISM: Homo Sapiens

<400> SEQUENCE: 25

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln Pro
    50                  55                  60

Pro Pro Pro Pro Pro Pro Pro Pro Pro Gln Leu Pro Gln Pro Pro
65                  70                  75                  80

Pro Gln Ala Gln Pro Leu Leu Pro Gln Pro Gln Pro Pro Pro Pro
                85                  90                  95

Pro Pro Pro Pro Pro Gly Pro Ala Val Ala Glu Glu Pro Leu His Arg
            100                 105                 110

Pro

<210> SEQ ID NO 26
<211> LENGTH: 114
<212> TYPE: PRT
<213> ORGANISM: Homo Sapiens

<400> SEQUENCE: 26

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln Gln
    50                  55                  60

Pro Pro Pro Pro Pro Pro Pro Pro Pro Pro Gln Leu Pro Gln Pro
65                  70                  75                  80

Pro Pro Gln Ala Gln Pro Leu Leu Pro Gln Pro Gln Pro Pro Pro Pro
                85                  90                  95

Pro Pro Pro Pro Pro Pro Gly Pro Ala Val Ala Glu Glu Pro Leu His
            100                 105                 110

Arg Pro

<210> SEQ ID NO 27
<211> LENGTH: 115
<212> TYPE: PRT
<213> ORGANISM: Homo Sapiens

<400> SEQUENCE: 27

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

```
Gln Gln Gln Gln Gln Gln Gln Gln Gln Gln Gln Gln Gln Gln Gln
        50                  55                  60
Gln Pro Pro Pro Pro Pro Pro Pro Pro Pro Gln Leu Pro Gln
 65                  70                  75                  80
Pro Pro Pro Gln Ala Gln Pro Leu Leu Pro Gln Pro Gln Pro Pro
                 85                  90                  95
Pro Pro Pro Pro Pro Pro Pro Gly Pro Ala Val Ala Glu Glu Pro Leu
            100                 105                 110
His Arg Pro
        115
```

<210> SEQ ID NO 28
<211> LENGTH: 116
<212> TYPE: PRT
<213> ORGANISM: Homo Sapiens

<400> SEQUENCE: 28

```
Ile Glu Gly Arg Gly Ile Arg Met Ala Thr Leu Glu Lys Leu Met Lys
 1               5                  10                  15
Ala Phe Glu Ser Leu Lys Ser Phe Gln Gln Gln Gln Gln Gln Gln
                20                  25                  30
Gln Gln Gln Gln Gln Gln Gln Gln Gln Gln Gln Gln Gln Gln
        35                  40                  45
Gln Gln Gln Gln Gln Gln Gln Gln Gln Gln Gln Gln Gln Gln Gln
        50                  55                  60
Gln Gln Pro Pro Pro Pro Pro Pro Pro Pro Pro Gln Leu Pro
 65                  70                  75                  80
Gln Pro Pro Pro Gln Ala Gln Pro Leu Leu Pro Gln Pro Gln Pro Pro
                 85                  90                  95
Pro Pro Pro Pro Pro Pro Pro Gly Pro Ala Val Ala Glu Glu Pro
            100                 105                 110
Leu His Arg Pro
        115
```

<210> SEQ ID NO 29
<211> LENGTH: 117
<212> TYPE: PRT
<213> ORGANISM: Homo Sapiens

<400> SEQUENCE: 29

```
Ile Glu Gly Arg Gly Ile Arg Met Ala Thr Leu Glu Lys Leu Met Lys
 1               5                  10                  15
Ala Phe Glu Ser Leu Lys Ser Phe Gln Gln Gln Gln Gln Gln Gln
                20                  25                  30
Gln Gln Gln Gln Gln Gln Gln Gln Gln Gln Gln Gln Gln Gln
        35                  40                  45
Gln Gln Gln Gln Gln Gln Gln Gln Gln Gln Gln Gln Gln Gln Gln
        50                  55                  60
Gln Gln Gln Pro Pro Pro Pro Pro Pro Pro Pro Pro Gln Leu
 65                  70                  75                  80
Pro Gln Pro Pro Pro Gln Ala Gln Pro Leu Leu Pro Gln Pro Gln Pro
                 85                  90                  95
Pro Pro Pro Pro Pro Pro Pro Pro Gly Pro Ala Val Ala Glu Glu
            100                 105                 110
Pro Leu His Arg Pro
        115
```

-continued

<210> SEQ ID NO 30
<211> LENGTH: 118
<212> TYPE: PRT
<213> ORGANISM: Homo Sapiens

<400> SEQUENCE: 30

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln Gln
    50                  55                  60

Gln Gln Gln Gln Pro Pro Pro Pro Pro Pro Pro Pro Pro Pro Pro Gln
65                  70                  75                  80

Leu Pro Gln Pro Pro Pro Gln Ala Gln Pro Leu Leu Pro Gln Pro Gln
                85                  90                  95

Pro Pro Pro Pro Pro Pro Pro Pro Pro Gly Pro Ala Val Ala Glu
            100                 105                 110

Glu Pro Leu His Arg Pro
        115

<210> SEQ ID NO 31
<211> LENGTH: 119
<212> TYPE: PRT
<213> ORGANISM: Homo Sapiens

<400> SEQUENCE: 31

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln Gln
    50                  55                  60

Gln Gln Gln Gln Gln Pro Pro Pro Pro Pro Pro Pro Pro Pro Pro Pro
65                  70                  75                  80

Gln Leu Pro Gln Pro Pro Gln Ala Gln Pro Leu Leu Pro Gln Pro Gln
                85                  90                  95

Gln Pro Pro Pro Pro Pro Pro Pro Pro Pro Gly Pro Ala Val Ala
            100                 105                 110

Glu Glu Pro Leu His Arg Pro
        115

<210> SEQ ID NO 32
<211> LENGTH: 120
<212> TYPE: PRT
<213> ORGANISM: Homo Sapiens

<400> SEQUENCE: 32

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
            20                  25                  30

Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln
    50                  55                  60

Gln Gln Gln Gln Gln Gln Pro Pro Pro Pro Pro Pro Pro Pro
65                  70                  75                  80

Pro Gln Leu Pro Gln Pro Pro Gln Ala Gln Pro Leu Leu Pro Gln
                85                  90                  95

Pro Gln Pro Pro Pro Pro Pro Pro Pro Pro Gly Pro Ala Val
            100                 105                 110

Ala Glu Glu Pro Leu His Arg Pro
        115                 120

<210> SEQ ID NO 33
<211> LENGTH: 121
<212> TYPE: PRT
<213> ORGANISM: Homo Sapiens

<400> SEQUENCE: 33

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln
            20                  25                  30

Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln
    50                  55                  60

Gln Gln Gln Gln Gln Gln Pro Pro Pro Pro Pro Pro Pro Pro
65                  70                  75                  80

Pro Pro Gln Leu Pro Gln Pro Pro Gln Ala Gln Pro Leu Leu Pro
                85                  90                  95

Gln Pro Gln Pro Pro Pro Pro Pro Pro Pro Pro Gly Pro Ala
            100                 105                 110

Val Ala Glu Glu Pro Leu His Arg Pro
        115                 120

<210> SEQ ID NO 34
<211> LENGTH: 122
<212> TYPE: PRT
<213> ORGANISM: Homo Sapiens

<400> SEQUENCE: 34

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln
            20                  25                  30

Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln
    50                  55                  60

Gln Gln Gln Gln Gln Gln Gln Pro Pro Pro Pro Pro Pro Pro
65                  70                  75                  80

Pro Pro Pro Gln Leu Pro Gln Pro Pro Gln Ala Gln Pro Leu Leu
                85                  90                  95

Pro Gln Pro Gln Pro Pro Pro Pro Pro Pro Pro Pro Gly Pro
            100                 105                 110

```
Ala Val Ala Glu Glu Pro Leu His Arg Pro
        115                 120

<210> SEQ ID NO 35
<211> LENGTH: 123
<212> TYPE: PRT
<213> ORGANISM: Homo Sapiens

<400> SEQUENCE: 35

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln Gln
    50                  55                  60

Gln Gln Gln Gln Gln Gln Gln Gln Pro Pro Pro Pro Pro
65                  70                  75                  80

Pro Pro Pro Pro Gln Leu Pro Gln Pro Pro Gln Ala Gln Pro Leu
                85                  90                  95

Leu Pro Gln Pro Gln Pro Pro Pro Pro Pro Pro Pro Pro Pro Gly
            100                 105                 110

Pro Ala Val Ala Glu Glu Pro Leu His Arg Pro
        115                 120

<210> SEQ ID NO 36
<211> LENGTH: 124
<212> TYPE: PRT
<213> ORGANISM: Homo Sapiens

<400> SEQUENCE: 36

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln Gln
    50                  55                  60

Gln Gln Gln Gln Gln Gln Gln Gln Gln Pro Pro Pro Pro Pro
65                  70                  75                  80

Pro Pro Pro Pro Pro Gln Leu Pro Gln Pro Pro Gln Ala Gln Pro
                85                  90                  95

Leu Leu Pro Gln Pro Gln Pro Pro Pro Pro Pro Pro Pro Pro Pro
            100                 105                 110

Gly Pro Ala Val Ala Glu Glu Pro Leu His Arg Pro
        115                 120

<210> SEQ ID NO 37
<211> LENGTH: 125
<212> TYPE: PRT
<213> ORGANISM: Homo Sapiens

<400> SEQUENCE: 37

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln Gln
```

```
                    20                  25                  30

Gln Gln Gln Gln Gln Gln Gln Gln Gln Gln Gln Gln Gln Gln
            35                  40                  45

Gln Gln Gln Gln Gln Gln Gln Gln Gln Gln Gln Gln Gln Gln
    50                  55                  60

Gln Gln Gln Gln Gln Gln Gln Gln Gln Pro Pro Pro Pro
65                  70                  75                  80

Pro Pro Pro Pro Pro Pro Gln Leu Pro Gln Pro Pro Gln Ala Gln
                85                  90                  95

Pro Leu Leu Pro Gln Pro Gln Pro Pro Pro Pro Pro Pro Pro
            100                 105                 110

Pro Gly Pro Ala Val Ala Glu Glu Pro Leu His Arg Pro
        115                 120                 125

<210> SEQ ID NO 38
<211> LENGTH: 55
<212> TYPE: PRT
<213> ORGANISM: Homo Sapiens

<400> SEQUENCE: 38

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln
            20                  25                  30

Gln Gln Gln Gln Gln Gln Gln Gln Gln Gln Gln Pro Pro Pro Pro
        35                  40                  45

Leu Glu Arg Pro His Arg Asp
    50                  55

<210> SEQ ID NO 39
<211> LENGTH: 86
<212> TYPE: PRT
<213> ORGANISM: Homo Sapiens

<400> SEQUENCE: 39

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln
            20                  25                  30

Gln Gln Gln Gln Gln Gln Gln Gln Gln Gln Gln Gln Gln Gln
            35                  40                  45

Gln Gln Gln Gln Gln Gln Gln Gln Gln Gln Gln Gln Gln Gln
    50                  55                  60

Gln Gln Gln Gln Gln Gln Gln Gln Gln Gln Pro Pro Pro Leu
65                  70                  75                  80

Glu Arg Pro His Arg Asp
            85

<210> SEQ ID NO 40
<211> LENGTH: 63
<212> TYPE: PRT
<213> ORGANISM: Homo Sapiens

<400> SEQUENCE: 40

Ile Glu Gly Arg Gly Ile Arg Met Ala Thr Leu Glu Lys Leu Met Lys
1               5                   10                  15

Ala Phe Glu Ser Leu Lys Ser Phe Gln Gln Gln Gln Gln Gln Gln
            20                  25                  30
```

```
-continued

Gln Gln Gln Gln Gln Gln Gln Gln Gln Gln Gln Pro Pro Pro Pro
            35                  40                  45

Leu Glu Gly Ile Phe Glu Ala Gln Lys Ile Glu Trp Arg Ser Pro
 50                  55                  60

<210> SEQ ID NO 41
<211> LENGTH: 94
<212> TYPE: PRT
<213> ORGANISM: Homo Sapiens

<400> SEQUENCE: 41

Ile Glu Gly Arg Gly Ile Arg Met Ala Thr Leu Glu Lys Leu Met Lys
 1               5                  10                  15

Ala Phe Glu Ser Leu Lys Ser Phe Gln Gln Gln Gln Gln Gln Gln
            20                  25                  30

Gln Gln Gln Gln Gln Gln Gln Gln Gln Gln Gln Gln Gln Gln Gln
            35                  40                  45

Gln Gln Gln Gln Gln Gln Gln Gln Gln Gln Gln Gln Gln Gln Gln
 50                  55                  60

Gln Gln Gln Gln Gln Gln Gln Gln Gln Gln Pro Pro Pro Pro Leu
65                  70                  75                  80

Glu Gly Ile Phe Glu Ala Gln Lys Ile Glu Trp Arg Ser Pro
                85                  90
```

COMPOSITION AND METHOD FOR THE DETECTION OF DISEASES ASSOCIATED WITH AMYLOID-LIKE FIBRIL OR PROTEIN AGGREGATE FORMATION

RELATED APPLICATIONS

This application claims priority to PCT/EP98/04811, filed on Jul. 31, 1998, which claims priority to European Patent Application 97113306.1, filed on Aug. 1, 1997.

FIELD OF THE INVENTION

The present invention relates to novel compositions useful for elucidating the onset or progress of diseases of preferably neuronal origin associated with the formation of amyloid-like fibrils or protein aggregates. Further, the present invention relates to methods for monitoring said formation as well as to methods for identifying inhibitors of said formation. Additionally, the invention relates to inhibitors identified by the method of the invention as well as to pharmaceutical compositions comprising said inhibitors.

BACKGROUND OF THE INVENTION

A variety of diseases, both in humans and animals, is characterized by the pathogenic formation of amyloid-like fibrils or protein aggregates in neuronal tissues. A well-known and typical example of such diseases is Alzheimer's disease (AD). AD is characterized by the formation of neurofibrillar tangles and β-amyloid fibrils in the brain of AD patients. Similarly, scrapie is associated with the occurrence of scrapie-associated fibrils in brain tissue.

Another class of these diseases is characterized by an expansion of CAG repeats in certain genes. The affected proteins display a corresponding polyglutamine expansion. Said diseases are further characterized by a late onset in life and a dominant pathway of inheritance.

A typical representative of this class of diseases is Huntington's disease. Huntington's disease (HD) is an autosomal dominant progressive neurondegenerative disorder characterized by personality changes, motor impairment and subcortical dementia (Harper, 1991). It is associated with a selective neuronal cell death occurring primarily in the cortex and striatum (Vonsattel et al., 1985). The disorder is caused by a CAG/polyglutamine (polygln) repeat expansion in the first exon of a gene encoding a large ~350 kDa protein of unknown function and designated huntingtin (HDCRG, 1993). The CAG repeat is highly polymorphic and varies from 6–39 repeats on chromosomes of unaffected individuals and 35–180 repeats on HD chromosomes (Rubinsztein et al., 1996; Sathasivam et al., 1997). The majority of adult onset cases have expansions ranging from 40–55 units, whereas expansions of 70 and above invariably cause the juvenile form of the disease. The normal and mutant forms of huntingtin have been shown to be expressed at similar levels in the central nervous system and in peripheral tissues (Trottier et al., 1995a). Within the brain, huntingtin was found predominantly in neurons and was present in cell bodies, dentrites and also in the nerve terminals. Immunohistochemistry, electron microscopy and subcellular fractionations have shown that huntingtin is primarily a cylosolic protein associated with vesicles and/or microtubules, suggesting that it plays a functional role in cytoskeletal anchoring or transport of vesicles (DiFiglia et al., 1995; Gutekunst et al., 1995; Sharp et al., 1995) Huntingtin has also been detected in the nucleus (de Rooij et al., 1996; Hoogeveen et al., 1993) suggesting that transcriptional regulation cannot be ruled out as a possible function of this protein.

In addition to HD, CAG/polygln expansions have been found in at least seven other inherited neurodegenerative disorders which include: spinal and bulbar muscular atrophy (SBMA), dentatorubral pallidoluysian atrophy (DRPLA), and the spinocerebellar ataxias (SCA) types 1, 2, 3, 6 and 7 (referenced in Bates et al. 1997). The normal and expanded size ranges are comparable with the exception of SCA6 in which the expanded alleles are smaller and the mutation is likely to act by a different route. However, in all cases the CAG repeat is located within the coding region and is translated into a stretch of polygln residues. Although the proteins harbouring the polygln sequences are unrelated and mostly of unknown function, it is likely that the mutations act through a similar mechanism. Without exception, these proteins are widely expressed and generally localized in the cytoplasm. However, despite overlapping expression patterns in brain, the neuronal cell death is relatively specific and can differ markedly (Ross, 1995), indicating that additional factors are needed to convey the specific patterns of neurodegeneration.

Several investigators have proposed that HD is caused by a toxic gain of function, which in turn is caused by abnormal protein—protein interactions related to the elongated polygln. It is possible that the binding of a protein to the polygln region could either confer a new property on huntingtin or alter its normal interactions causing selective cell death either through the specific expression patterns of the interacting protein or through the selective vulnerability of certain cells. To date, four potential huntingtin-interacting proteins have been isolated: 1 (Li et al., 1995), GAPDH (Burke et al., 1996), HIP2 (Kalchman et al., 1996) and HIP-I (Kalchman et al.,: 1997; Wanker et al., 1997). However, it has not been demonstrated whether the binding of these proteins to huntingtin is involved in the selective neuropathology. A gain of function mechanism has been supported by the identification of an antibody that specifically reacts with the pathogenic polygln expansions (Trottier et al., 1995b) This indicates that upon expansion into the pathogenic range, a polygln sequence may undergo a conformational change. Poly-L-glutamines form pleated sheets of β-strands held together by hydrogen bonds between their amides (Perutz et al., 1994). It was proposed that the expanded glutamine repeats in huntingtin may function as polar zippers, joining protein molecules together (Perutz, 1996). In the long run, this could result in the precipitation of huntingtin protein in specific neurons causing the observed selective neuronal loss. Thus, the mechanism underlying HD would be similar to scrapie, Creutzfeldt-Jakob or Alzheimer's disease, in which β-sheet secondary structures lead to the formation of toxic protein aggregates in selective neurons (Caughey and Chesebro, 1997).

Recently, strains of mice (R6) that are transgenic for the HD mutation have been generated (Mangiarini et al., 1996). In these mice exon 1 of the human HD gene carrying CAG repeat expansions of 115–156 units is expressed under the control of the human HD promoter. It has been demonstrated that the transgenic animals exhibit a progressive neurological phenotype that exhibits many of the motor and non motor features of HD. The phenotype includes a resting tremor; irregular gait; rapid, abrupt shuddering movements; stereotypic grooming movements and epileptic seizures. Coincident with the onset of the movement disorder the mice show a progressive weight loss. Neuropathological analysis has shown a reduction in brain weight (which precedes that in body weight) and the presence of neuronal intranuclear inclusions (NIIs) predating any evidence of neuronal dysfunction (Davies et al., 1997). The NIIs are immunoreactive for N-terminal huntingtin antibodies that detect the transgene protein and for ubiquitin but do not contain the endogenous mouse huntingtin. At the ultrastructural level, a solitary intranuclear inclusion appears as a roughly circular pale structure of a fine granular nature with occasional filamentous structures and devoid of a membrane. In addition, the neurons invariably have indentations of the nuclear membrane and an apparent increase in the density and clustering of nuclear pores. All three of these ultrastructural nuclear changes have previously been reported in EM studies from HD patients (Roizin et al., 1979; Roos and Bots, 1983; Tellez-Nagel et al., 1974).

Thus, a large body of data has accumulated that describes aspects of the pathology of the above-discussed diseases. However, the actual mechanisms leading to the onset of the various disease states are still unknown. Although a variety of hypotheses have been formulated in the art, it is equally unknown how the amyloid or aggregate formation is triggered or caused within affected cells or tissues. Without a detailed knowledge of the formation of said aggregates, the development of a suitable pharmaceutical composition for treating such diseases appears rather difficult. The technical problem underlying the present invention was therefore to provide means and methods suitable for the eventual elucidation of the etiology of these diseases and the development of appropriate medicines.

SUMMARY OF THE INVENTION

The above technical problem is solved by the embodiment characterized in the claims. Accordingly, the present invention relates to a composition comprising:
  (a) a nucleic acid molecule encoding a fusion protein comprising:
    (aa) a (poly)peptide that enhances solubility and/or prevents aggregation of said fusion protein; and
    (ab) an amyloidogenic (poly)peptide that has the ability to self-assemble into amyloid-like fibrils or protein aggregates;
  (b) a vector containing the nucleic acid molecule of (a);
  (c) a host transformed with the vector of (b);
  (d) a fusion protein encoded by the nucleic acid of (a) or a functional derivative thereof; and/or
  (e) an antibody specific for the fusion protein of (d).

As used herein, the term "(poly)peptide" relates to a polypeptide or a peptide depending on the length of the amino acid string. Said (poly)peptide has the ability to enhance solubility of a fusion partner in said fusion protein and thus of the fusion protein itself. Additionally, or alternatively, said (poly)peptide prevents the aggregation of the fusion partner and thus of the fusion protein. Said (poly)peptide is combined within said fusion protein with an amyloidogenic (poly)peptide having the above recited features. The connection of both (poly)peptides may be via a linker or by a direct attachment. It is preferred that either the linker or either (poly)peptide comprises a cleavable site. Said cleavable site should render both (poly)peptides essentially intact. Alternatively, said fusion protein may comprise a number of cleavage sites. Upon cleavage, which may be exhaustive or under limiting conditions, the amyloidogenic (poly)peptide should, when used for the purposes of the present invention, retain the ability to self-assemble. The person skilled in the art is in the position to determine appropriate conditions for a corresponding limited cleavage. The composition of the invention may comprise one, several, or all of the compounds recited in features (a) to (e), above.

The term "functional derivative" refers to a fusion protein which comprises, for example, modified amino acids or amino acid substitutions and retains the functions of the fusion protein detailed herein above.

The term "antibody specific for the fusion protein" comprised in the composition of the invention is intended to mean that said antibody is only specific for the fusion protein but not for either of the above cited components of said fusion protein.

In accordance with the present invention, it could surprisingly be shown that the composition comprising the above recited components can be used for the elucidation of amyloid-like fibril or protein aggregate formation. The components of the composition can be used in varying combinations to test, for example, for specific conditions under which amyloids are formed in vitro. The in vitro data obtained with the composition of the invention may then be compared to or brought into relation with the in vivo situation and appropriate conclusions may be drawn therefrom.

The in vitro systems that can be established with the composition of the invention allow formation of highly stable amyloid-like protein aggregates. Such aggregates may be obtained, for example, by proteolytic cleavage of GST fusion proteins comprising exon 1 of the HD gene and containing expanded polygln sequences. Alternatively, such aggregates may be obtained by lowering the pH value from 8 to 5 or by increasing the protein concentration. The arrays of fibrillar structures of varying sizes and shapes observed by electron microscopy surprisingly clearly resemble those of purified amyloids. Furthermore, the polarization microscopic properties of the fibrils stained with Congo red are strikingly similar to those described for amyloids. The green-gold birefringence of the amyloid-like fibrils indicates that the polymers have common structural features. Although the Congo red staining does not determine conclusively whether the fibrils consist of β-pleated sheets, the method suggests that this is likely in view of experience gained with other protein polymers (Caputo et al., 1992). However, it has been generally accepted that naturally occurring mammalian protein polymers that exhibit fibrillar structures and green birefringence after Congo red staining should be classified as amyloids (Glenner, 1980). Instead of the HD gene, other nucleic acid sequences encoding amyloidogenic (poly)peptides may be used to generate said fusion proteins. Preferably, the composition of the invention is a diagnostic composition. The composition of the invention may also be a kit. The diagnostic composition can advantageously be employed in the assessment of a disease state whereas the kit may rather be employed in the development of, for example, inhibitors or in the elucidation of amyloid formation.

It is a preferred embodiment of the composition of the invention, that said amyloidogenic (poly)peptide comprises a polyglutamine expansion. In the prior art it has been shown by X-ray diffraction studies that synthetic peptides containing polyglns form β-sheets strongly held together by hydrogen bonds (Perutz et al., 1994). Because synthetic poly(L-glutamine) is insoluble in water, a synthetic peptide with the sequence $Asp_2$-$Gln_{15}$-$Lys_2$ was used in that study. A stretch of 10 glutamines was also inserted into the loop of chymotrypsin inhibitor-2 (CI2), and it was demonstrated by analytical ultracentrifugation that the recombinant protein, in addition to monomers formed dimers and trimers, whereas wild-type Cl2 was present only in the monomeric form (Stott et al., 1995). It has been proposed that the polygln stretch functions as a polar zipper, joining proteins together. However, the hypothesis that glutamine repeats in proteins form β-pleated sheets and induce protein aggregation by a mechanism similar to that observed in spongiform encephalopathy (TSE) diseases (Caughey and Chesebro, 1997) could not be proven with this recombinant protein. Most likely, the length of the polygln sequence inserted into Cl2 was too short. Accordingly, the experimental data actually obtained teach away from the above recited hypothesis.

In a particularly preferred embodiment said polyglutamine expansion comprises at least 35 glutamines. In a further particularly preferred embodiment said polyglutamine expansion comprises at least 51 glutamines.

Figure 3:
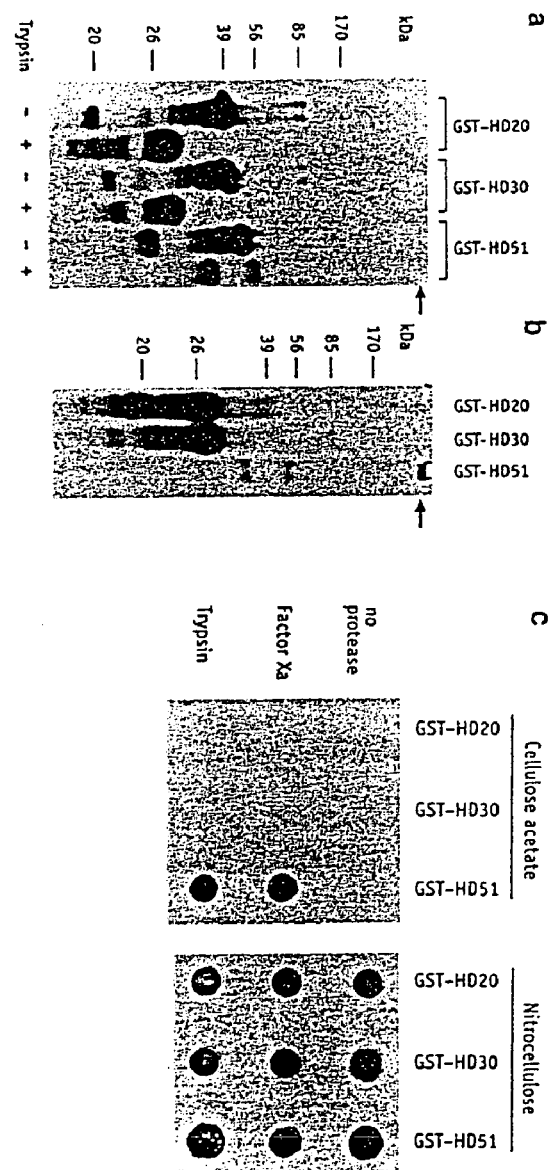
Figure 4:
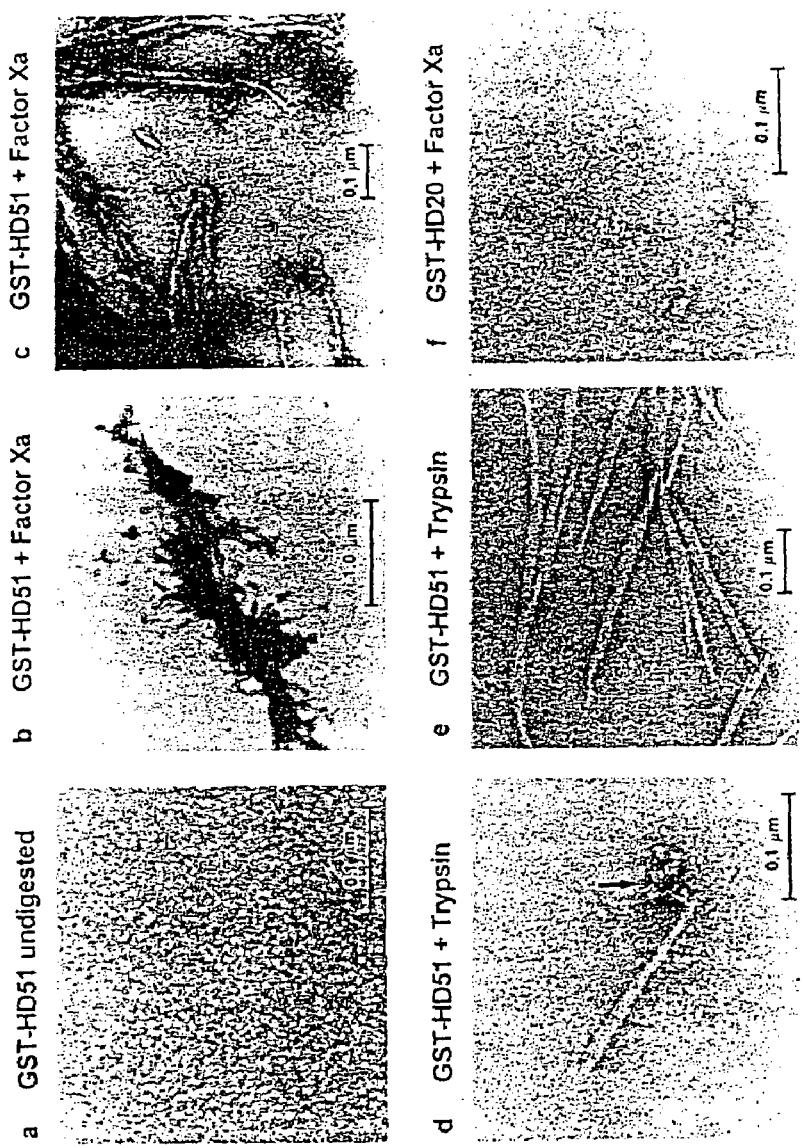

Our studies with the GST-HD fusion proteins containing polygln sequences of varying lengths demonstrate that a certain length of the polygln stretch is necessary for the formation of amyloid-like fibrils in vitro. When the purified fusion proteins were analyzed by SDS-PAGE, insoluble high molecular weight protein aggregates were only detected with the proteins containing 81 and 122 glutamines (FIGS. 1a and b), whereas the protein with 51 glutamines was soluble and no fibrillar structures were detected by electron microscopy (FIG. 4a). This indicates that the critical length of the polygln stretch in the fusion proteins leading to the formation of aggregates is greater than 51 glutamines. Accordingly, fusion proteins of the invention with a polyglutamine expansion of more than 51 glutamines, such as 81 or 122 glutamines, may be employed in studies for the formation of aggregates that render a cleavage reaction unnecessary. However, when the GST-tag, which is known to enhance the solubility of many proteins (Smith and Johnson, 1988), was cleaved by limited digestion with trypsin, the liberated HD exon 1 protein with 51 glutamines also started to form aggregates (FIG. 3a) and the amount of these aggregates increased when the GST-tag was totally degraded with trypsin (FIG. 3b). This indicates that in the HD exon 1 protein 51 glutamines are sufficient to form aggregates, whereas 20 and 30 glutamines under the same conditions are not. The minimum critical length essential for the development of amyloid-like structures after removal of the GST-tag is not known and has to be determined. However, preliminary experiments in our laboratory suggest that the threshold for the formation of HD exon 1 protein aggregates is between 35–48 glutamines. This result is strikingly similar to the pathological threshold in HD, SBMA, DRPLA, SCA1, SCA2, SCA3 and SCA7. In all of these neurodegenerative polygln diseases a pathological phenotype was found when more than 41 repeats were present, suggesting that the elongation of the polygln repeat beyond a certain length may lead to a phase change in the affected proteins. This could, for example, be a change from random coils to hydrogen-bonded hairpins in the polygln stretch, see Perutz (1996).

Figure 7:
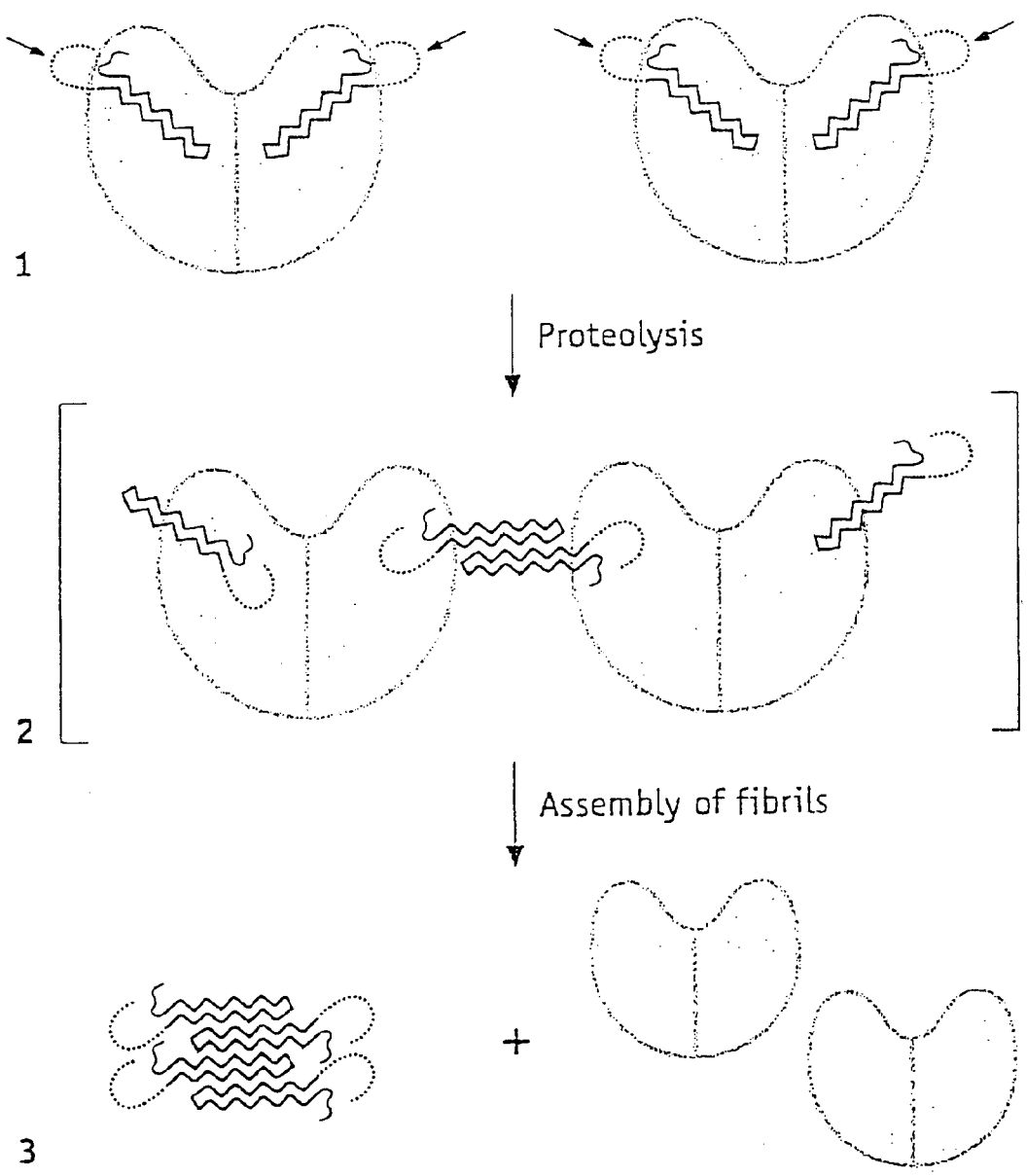

With the understanding that the applicant is not bound by any scientific theory, a mechanism is proposed for the fibril formation induced by proteolytic: cleavage of GST-HD51 as shown in FIG. 7. Based on the known crystal structure of GST with a C-terminal fusion peptide (Lim et al., 1994) and the fact that the purified GST protein is a dimer we suppose that native GST-HD51 exists as a dimer with two expanded polygln sequences which form stable hairpins consisting of antiparallel β-strands strongly held together by hydrogen bonds between the main chain and the side chain amides. In the native protein both hairpins are tightly bound to the surface of GST and not accessible for protein—protein interactions with other polygln sequences. As a result of the cleavage with a site-specific protease, both hairpins become accessible and β-sheets with hairpins from other cleaved protein molecules are formed. This transient population of intermediates consisting of GST molecules and hairpins leads to the formation of polygln-containing β-sheet fibrils and free GST molecules. This model is supported by the finding of potential intermediate structures present on one or both ends of the growing fibrils (FIGS. 4c and d). These clots of varying sizes were not detected when GST-HD51 was digested to completion with trypsin, which totally degrades the GST-tag, whilst they were detectable upon limited digestion, leaving the GST moiety largely intact (FIG. 4d). This indicates that these structures are transient intermediates.

A model of the formation of amyloid-like fibrils via transient intermediates is not without precedent. Booth et al. (1997) have shown that amyloidogenic lysosome variants aggregate on heating, unlike the wild-type protein, and that the lysozyme fibrils are formed from potential precursor proteins. It is possible that the transient GST-HD intermediates function as nuclei for ordered protein aggregation, very similarly to protein crystallization and microtubule formation, which are nucleation-dependent polymerisations (Jarrett and Lansburry, 1993). Once a nucleus is formed, the further addition of monomers becomes thermodynamically favorable and results in rapid polymerization. An important feature of a nucleation-dependent process is a lag time before the aggregates are detectable. During this period, dimers and trimers are formed. FIG. 3a shows that during proteolytic cleavage of GST-HD51 dimers of the released HD portion are formed, the concentration of which then decreases upon prolonged incubation concomitant with an increase in the formation of large protein aggregates (FIG. 3b). Although additional kinetic studies will be necessary to prove this assumption, preliminary results in our laboratory suggest that a "one-dimensional" crystallization leads to the formation of in vitro amyloid-like huntingtin aggregates.

Accordingly, the present invention provides both the possibilities to analyze aggregation of amyloid-like aggregates using defined cleavage conditions or using fusion proteins comprising long polyglutamine stretches that render the cleavage unnecessary. Whereas the cleavage of the fusion protein enables to set a distinct starting point of the reaction and therefore of the aggregate formation, the second alternative has the advantage that the use of a cleaving agent is rendered obsolete.

In a further particularly preferred embodiment of the invention said (poly)peptide defined in (ab) is huntingtin, androgen receptor, atropin, TATA binding protein, or ataxin-1, -2, -3, -6 or -7 or a fragment or derivative thereof.

The fibrillar structures formed by proteolytic cleavage of purified GST-HD51 in vitro and also in the brains of mice transgenic for the HD mutation are very similar to structures detected in brain sections or purified protein fractions of Alzheimer's disease (AD), Creutzfeldt-Jakob disease (CJD), Parkinson's Disease, Gerstmann-Strätssler-Scheinker syndrome (GSS), fatal familial isomnia (FFI), kuru, bovine spongiform encephalopathy (BSE) and scrapie (Caughey and Chesebro, 1997). In all these disorders, the accumulation of amyloid-like fibrils in the central nervous system is accompanied by loss of nerve cells and a neuropathological phenotype. However, the molecular basis of these diseases is not known. For the first time, our results raise the possibility that HD, DRPLA, SBMA, SCA1, SCA2, SCA3 and SCA7 are also the result of a toxic amyloid fibrillogenesis. Although the detection of amyloid-like fibrils has not previously been reported in these inherited diseases, our results strongly suggest that polygln-containing polymers are also formed in vivo by their detection in a transgenic model of polyglutamine disease. The high molecular weight aggregates were exclusively detected in the nuclear fraction prepared from transgene brain material, which is in good agreement with the results of Davies et al. (1997), who demonstrated the presence of the transgene protein and ubiquitin in neuronal intranuclear inclusions, from a time prior to the development of a neurological phenotype. Strikingly, ultrastuctural analysis has shown similar intranuclear inclusions to be present in the cortical and striatal biopsy material from HD patients (Roizin et al., 1979) some of which showed clear evidence of intranuclear fibrils of up to 1 µm in length. Preliminary experiments with nuclear protein fractions prepared from HD brain material indicated that insoluble huntingtin aggregates are indeed present in these fractions. However, additional control experiments have to be performed to substantiate these results.

One possible explanation for the absence of detection of high molecular weight huntingtin protein aggregates in HD brains could be that the aggregates consist mainly of polygln-containing peptides which have been cleaved from the full length protein. In such a case, only an antibody raised against an N-terminal huntingtin fragment, containing the polygln sequence, would be able to detect the aggregates in the nucleus. In most of the previous immunohistochemical studies, antibodies raised against the central or C-terminal portion of huntingtin have been used, which detect the full length protein (350 kDa) in the cytosol and in the membrane containing fractions (DiFiglia et al., 1995; Sharp et al., 1995; Trottier et al., 1995a). However, antibodies raised against peptides and fusion proteins from the N- and C-terminus of huntingtin also detected the protein in the nucleus (de Rooij et al., 1996; Hoogeveen et al., 1993), indicating that huntingtin is also present in this subcellular compartment. There are several lines of evidence to implicate a shorter polygln-containing peptide/protein fragment of huntingtin in the pathology of HD. Ikeda et al. (1996) showed that a short fragment of the MJD1 protein containing 79 polyglns (Q79C) but not the full length protein with the elongated repeat induced apoptotic cell death in COS cells. The polygln-containing protein fragment migrated in SDS-gels at a position much higher than expected from its molecular weight, even after boiling in the presence of 2% SDS. These results are in good agreement with our data obtained using the GST-HD fusion proteins containing elongated polygln sequences. FIGS. 1a and b show that the expression of GST-HD83 and GST-HD122 in E. coli was dramatically reduced compared to the fusion proteins containing 20–51 repeats, and additional studies have indicated that the elongated glutamines are toxic for E. coli cells.

The possibility that polygln-containing cleavage products of huntingtin cause neurodegeneration in HD is substantiated by the finding of Goldberg et al. (1996) who showed that an N-terminal 80 kDa huntingtin fragment is cleaved from the full length protein by apopain, a proapoptotic cysteine protease. This indicates that the N-terminus of huntingtin is primarily accessible for proteases and distinct proteolytic cleavage products can be formed in vitro and in vivo. In addition, there is strong evidence that the mutated huntingtin somehow induces apoptotic cell death in HD, but the underlying molecular mechanism is not known (Duyao et al., 1995; Portera-Cailliau et al., 1995). Our data suggest that a proteolytic cleavage product of huntingtin, which is transported into the nucleus by an unknown mechanism, causes selective neuronal cell death by the formation of insoluble amyloid-like fibrils. It is possible that the transport to the nucleus is facilitated by a specific nuclear transport mechanism which is unique to certain neuronal cells and involves abnormal protein—protein interactions related to the elongated polygln. Alternatively, there may be specific nuclear proteins in the affected neurons which enhance the huntingtin protein aggregation.

Recently, the formation of neuronal intranuclear inclusions in mice transgenic for the SCA1 mutation have been detected, indicating that polygln-containing polymers are also formed in spinocerebellar ataxia type 1. Furthermore, the accumulation of polyglutamine-containing protein aggregates in neuronal intranuclear inclusions (NIIs) has been demonstrated for several progressive neurodegenerative diseases such as Huntington's disease (HD) (M. DiFiglia et al., 1997; M. W. Becher et al., 1997), dentatorubral pallidoluysian atrophy (DRPLA) (M. W. Becher et al., 1997; S. Igarashi et al., 1998) and the spinocerebellar ataxia (SCA) types 1 (P. J. Skinner et al., 1997; A. Matilla et al., 1997), 3 (H. L. Paulson et al., 1997) and 7 (M. Holmberg et al., 1998).

The components of the composition of the invention may be packaged in containers such as vials, optionally in buffers and/or solutions. If appropriate, one or more of said components may be packaged in one and the same container.

In an additional preferred embodiment of the composition of the present invention, said amyloidogenic (poly)peptide self-assembles subsequent to release from said fusion protein.

As has been pointed out herein before, the self-assembly of said (poly)peptides only subsequent to the release from the fusion protein provides the advantage that an exact time point of the start of the formation can be set. This has a number of advantages. For example, inhibitors of aggregate formation can be tested as regards their efficacy as a function of time. In addition, obtainment of data is facilitated in view of the fact that for amyloid formation a premix may be set up to which only the cleaving agent must be added.

In a further preferred embodiment of the composition of the invention, said amyloidogenic (poly)peptide is the amyloid precursor protein (APP), β-protein, an immunoglobulin light chain, serum amyloid A, transthyretin, cystatin C, β2-microglobulin, apolipoprotein A-1, gelsoline, islet amyloid polypeptide (IAPP), calcitonin, a prion, atrial natriuretic factor (ANF), lysozyme, insulin, fibrinogen, tau proteins or α-synuclein or a fragment or derivative thereof.

Deposits of β-amyloid in neuritic plaques and blood vessel walls are the principal pathological feature in the brains of patients with Alzheimer's disease. These amyloid deposits contain the 39–43 amino acid β-amyloid peptide which is derived by proteolytic cleavage from the larger precursor, the amyloid precursor protein (APP). There is strong evidence that the formation and aggregation of β-amyloids into fibrils is the primary pathogenic event leading to amyloid deposition in Alzheimer's disease.

An additional preferred embodiment relates to a composition wherein said (poly)peptide defined in (aa) is glutathione S-transferase (GST), intein, thioredoxin, dihydrofolate reductase (DHFR) or chymotrypsin inhibitor 2 (CI2) or a functional fragment or derivative thereof.

All of these (poly)peptides may be advantageously used to enhance the solubility and/or prevent aggregation of the fusion proteins of the invention. Particularly preferred is to employ intein in said composition because the protein has been modified such that it undergoes a self-cleavage reaction at its N-terminus at low temperatures in the presence of thiols such as DTT (MPACT™ I System/New England Biolabs). Also comprised by this embodiment are functional fragments of any of these above recited proteins. The term "functional fragment" as used herein is intended to denote the capability of said fragment to confer solubility or prevent aggregation.

Further preferred is that the nucleic acid contained in the composition of the invention is DNA. Particularly preferred is that said DNA is cDNA, synthetic DNA or (semi)synthetic DNA.

Also preferred is that the vector that may be contained in the composition of the invention is an expression vector or a gene targeting vector. These vectors may advantageously be used for transfecting hosts that may or may not be contained in the composition of the invention.

Such vectors may comprise further genes such as marker genes which allow for the selection of said vector in a suitable host cell and under suitable conditions. Preferably, the nucleic acid molecule of the invention is operatively linked to expression control sequences allowing expression in prokaryotic or eukaryotic cells. Expression of said nucleic acid molecule comprises transcription of the nucleic acid molecule into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the nucleic acid molecule. Furthermore, depending on the expression system used leader sequences capable of directing the polypeptide to a cellular compartment or secreting it into the medium may be added to the coding sequence of the nucleic acid molecule of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (In-vitrogene), or pSPORT1 (GIBCO BRL). Preferably, the expression control sequences will be eukaryotic promoter systems in vectors capable of transforming or transfecting eukaryotic host cells, but control sequences for prokaryotic hosts may also be used.

Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534–539; Schaper, Circ. Res. 79 (1996), 911–919; Anderson, Science 256 (1992), 808–813; Isner, Lancet 348 (1996), 370–374; Muhlhauser, Circ. Res. 77 (1995), 1077–1086; Wang, Nature Medicine 2 (1996), 714–716; WO94/29469; WO 97/00957 or Schaper, Current Opinion in Biotechnology 7 (1996), 635–640, and references cited therein. The nucleic acid molecules and vectors of the invention may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell.

Said hosts may then be used for the production of the fusion protein comprised in the composition of the invention.

Said host cell may be a prokaryotic or eukaryotic cell. The nucleic acid molecule or vector of the invention which is present in the host cell may either be integrated into the genome of the host cell or it may be maintained extrachromosomally.

Preferably, said host is a bacterial, preferably an *E. coli*, an animal-, preferably a mammalian, an insect-, a plant-, a fungal, preferably a yeast- and most preferably a *Saccharomyces* or *Aspergillius* cell, a *Pichia pastoris* cell, a transgenic animal or a transgenic plant.

The present invention also relates to a method of producing a fusion protein as defined in the diagnostic composition of any of the preceding claims comprising culturing or raising the host as defined in claim 11 and isolating said fusion protein. Preferably the bacterial host *E. coli* is used for the expression of the GST-HD fusion proteins. The cDNA fragments containing CAG repeats in the normal or pathological range may, for example, be cloned into pGEX-5X-1 (Pharmacia) and the resulting plasmids expressing fusion proteins with polygln-sequences used for protein purification. The resulting proteins may be purified under native conditions by affinity chromatography on glutathione agarose (Smith and Johnson, 1988).

Additionally, the present invention relates in a preferred embodiment to a composition wherein said antibody is a monoclonal antibody, polyclonal antibody, phage display antibody or a fragment or derivative thereof.

The above recited fragments or derivatives comprise Fv-, Fab-, F(ab)'$_2$-fragments, single-chain antibodies or single-chain antibody domains. These antibodies may advantageously be used in experiments such as Western blotting experiments to determine the presence of the protein on, for example, nitrocellulose membrane.

Alternatively, the antibody, derivative or fragment thereof may be used in immunometric assays such as ELISAs or RIAs or may be coupled to columns in order to retain the fusion protein from, for example, mammalian sources on said column for further detection or purification.

Alternative uses and advantages of the antibody or fragment or derivative contained in the composition of the invention are, on the basis of the teachings of this invention, clear to the person skilled in the art.

The invention further relates to an in vitro method of producing amyloid aggregates comprising (a) at least partially cleaving the fusion protein comprised in the diagnostic composition of the invention wherein the (poly)peptide that is released has the ability to self-assemble into amyloid-like fibrils or protein aggregates or (b) inducing self-assembly into amyloid-like fibrils or protein aggregates by heating the fusion protein comprised in the composition of the present invention or an amyloidogenic (poly)peptide that has a ability to self-assemble into amyloid-like fibrils or protein aggregates by inducing a pH change in a solution comprising said fusion protein/(poly)peptide or by treating said fusion protein/(poly)peptide with a denaturing agent.

The method of the invention may advantageously be used to study in more detail the process that leads to the formation of amyloid-like fibrils or protein aggregates from amyloidogenic (poly)peptides. Using the method of the invention, the onset of, for example, HD or AD can be examined in an in vitro situation. It is important that the polypeptide that is released by the cleaving agent still retains the possibility to form amyloid-like fibrils or protein aggregates. The formation of such fibrils or aggregates may be monitored, for example, by electron or light microscopy. Varying the cleaving conditions in cases where more than one cleavage site is present on the fusion protein may be used to further elaborate the minimal requirements for said amyloid-like fibril or protein aggregate formation.

Preferably, the cleavage is effected chemically or enzymatically, or by the intein self-cleavage reaction in the presence of thiols.

In the following, enzymatic cleavage will also be referred to as proteolytic cleavage. The enzymatic cleavage has the advantage that the cleavage reaction can be performed under almost physiological conditions and normally only low amounts of the protease are necessary for the cleavage reaction. Furthermore, said cleavage is highly specific and the enzyme can be regarded as nontoxic. Therefore, one can envisage a wide variety if applications within this invention. The disadvantage of the enzymatic cleavage reaction is that prospective inhibitors might inhibit in some cases the protease and in turn prevent the formation of protein aggregates. In comparison, this is not the case when the cleavage reaction is performed chemically.

Further, the present invention relates to a method of testing a prospective inhibitor of aggregate formation of a fusion protein as defined in the composition of the invention when enzymatically or chemically cleaved or a non-cleaved fusion amyloidogenic (poly)peptide as defined hereinbefore or an amyloidogenic non-fusion (poly)peptide comprising (a) incubating in the presence of a prospective inhibitor (aa) said fusion protein in the presence or absence of a cleaving agent; or (ab) said non-fusion poly(peptide); and (b) assessing the formation of amyloid-like fibrils or protein aggregates.

This method of the present invention provides a particularly strong impact on the pharmaceutical research related to amyloid-associated diseases. For the first time, an inhibitor of fibril or aggregate formation can conveniently, directly, easily and within a short time be tested in vitro. As has been detailed herein above, aggregate formation may be tested on cleavage products, on non-cleaved fusion proteins or on the above recited non-fusion proteins which have the capacity to aggregate when the temperature is raised, the pH is lowered or the protein is dissolved in urea and the urea is slowly diluted out with a solvent. Additionally, the present invention does not exclude self-assembly under different conditions.

It was shown recently that acid-mediated denaturation of, e.g., transthyretin yields a conformational intermediate that can self-assemble into amyloid (Lai et al., 1996). Booth et al. demonstrated that heat denaturation of human lysozyme variants resulted in instability, unfolding, and amyloid fibrillogenesis.

Preferably, the incubation is effected in the presence of factor Xa, trypsin, endoproteinase Arg-C, endoproteinase Lys-C, proteinase K, thrombin or elastase at a temperature of preferably 25 to 37° C. for 0,5 to 16 hours and the assessment of the formation of fibrils or aggregates in step (b) is preferably effected by a filter assay or by a thioflavine T (ThT) fluorescence assay, in which the fluorescence intensity reflects the degree of aggregation.

As regards the filter assay, a more detailed protocol thereof is explained in the European patent application entitled "Novel method of detecting amyloid-like fibrils or protein aggregates" filed on the same day with the European Patent Office and assigned to the same applicant which is explicitly incorporated herein by reference.

Additionally, the present invention relates to a method for identifying an inhibitor of aggregate formation of a fusion protein as defined in the invention prior to or after proteolytic or chemical cleavage or of a non-fusion amyloidogenic (poly)peptide as described herein above comprising (a) loading a surface or gel with said protein or an aggregate thereof;

(b) incubating said surface or gel with a prospective inhibitor; and (c) assessing whether the presence of said prospective inhibitor avoids or reduces aggregate formation or further aggregate formation.

In accordance with this embodiment of the invention, proteolytic or chemical cleavage can be advantageously effected either prior or after the loading of the surface or gel leaving the investigator additional degrees of freedom in devising his experiments. The method of the invention is both useful for investigating the onset of aggregate or fibril formation or assessing the progression of such a process starting from the already existing aggregate or fibril. The latter embodiment is particularly useful in investigating treatment conditions for patients that are already affected by the disease at an early or medium stage thereof.

There is strong evidence that the formation of amyloids is a nucleation-dependent polymerization similar to protein crystallization or microtubule assembly. However, the deposition of a monomer onto a preexisting amyloid template is independent of the nucleation process. Thus, it will be very important to study the deposition of monomers onto a defined template under physiological conditions. With our in vitro system we should be able to monitor the deposition of radiolabelled polygln-containing monomers.

Preferably, said surface employed in the method of the invention is a membrane. Preferably, the membrane should be cellulose acetate and should have a low binding capacity for soluble proteins.

The invention also relates to an inhibitor identifiable or identified by the method of the invention.

The various methods described herein above will give rise to the isolation of a number of inhibitors which are also comprised by the present invention. Once such an inhibitor is known, it is of course not necessary to identify it again by the method of the invention. Rather, said inhibitor can be produced by chemical or recombinant means. In the case that the inhibitor is of proteinaceous material, it is preferred to resynthesize a compound having the or most of the characteristics of said inhibitor by peptidomimetics.

Preferably, a number of compounds or compound classes are tested for their efficacy to inhibit amyloid-like fibril or protein aggregate formation. Said compounds comprise an antibody, 4'-Iodo-4'-deoxydoxorubicin (IDOX), pyronine Y, guanidine hydrochloride, urea, rifampicin and derivatives thereof, myristyltrimethylammonium bromide, hydroquinone, p-benzoquinone, 1,4-dihydroxynaphthalene, p-methoxyphenol, α-tocopherol, ascorbic acid, β-carotene, anthracycline, doxorubicin, hexadecyl-N-methylpiperidinium, dodecyltrimethyl-ammonium, N-tetradecyl-N,N-dimethyl-3-ammonio-1-propanesulfonate, a (poly)peptide, glutamine or an oligoglutamine peptide. These compounds may be used in the inhibition or reversion of aggregate formation, for example, by formulation into a pharmaceutical composition for the treatment of any of the diseases cited herein.

The present invention also relates to a pharmaceutical composition comprising the inhibitor of the invention and a pharmaceutically acceptable carrier and/or diluent.

The pharmaceutical composition of the invention will find wide applicability in the medical field. Essentially all diseases associated with protein aggregate formation or amyloid-like fibril formation, in particular if they are associated with neuronal tissue or cells, may be effectively treated with the pharmaceutical composition of the invention.

Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery.

The therapeutically useful compounds identified according to the method of the invention may be administered to a patient by any appropriate method for the particular compound, e.g., orally, intravenously, parenterally, transdermally, transmucosally, or by surgery or implantation (e.g., with the compound being in the form of a solid or semi-solid biologically compatible and resorbable matrix) at or near the site where the effect of the compound is desired.

Finally, the present invention relates to a transgenic mammal or plant comprising a nucleic acid molecule or vector as described in the invention. The transgenic mammal or plant would advantageously be used for the in vivo testing of the efficacy of the inhibitors referred to above. With the pharmaceutical composition of the invention the formation of protein aggregates in the brain or other tissues of a transgenic animal can be monitored quantitatively. Furthermore, in vivo studies relating to the onset or progress of the above recited diseases may be carried out.

DESCRIPTION OF FIGURES AND EMBODIMENTS

FIG. 1

SDS-PAGE Analysis of Purified GST and GST-HD Fusion Proteins.

(a) Aliquots (15 ml) of eluates from the glutathione agarose column were subjected to 12.5% SDS-PAGE and analyzed by staining with Coomassie blue R. Lanes 1–6 contain GST, GST-HD20, -HD30, -HD83 and -HD122, respectively; lane M contains molecular mass standards. (b) Proteins were transferred to nitrocellulose and probed with anti-HD1 antibody. Arrows mark the origin of electrophoresis.

FIG. 2

Structure of GST-HD Fusion Proteins

The amino acid sequence (SEQ ID NO:6) corresponding to exon 1 of huntingtin is boxed. Arrows labeled Xa and T indicate cleavage sites for factor Xa and trypsin, respectively.

FIG. 3

Site-Specific Proteolysis of GST-HD Fusion Proteins with Trypsin and Factor Xa.

Tryptic digestions were performed at 37° C. for 3 (a) or 16 h (b). Native proteins and their cleavage products were subjected to 12.5% SDS-PAGE, blotted onto nitrocellulose membranes, and probed with anti-HD1 antibody. Arrows mark the origin of electrophoresis. (c) Purified fusion proteins and their factor Xa and trypsin cleavage products were analyzed using the filter retardation assay. The proteins retained by the cellulose acetate and nitrocellulose membranes were detected by incubation with the anti-HD1 antibody.

FIG. 4

Electron Micrographs of Native GST-HD Fusion Proteins and their Factor Xa and Trypsin Cleavage Products.

Purified GST fusion proteins were protease treated, negatively stained with uranyl acetate and viewed by electron microscopy. The undigested GST-HD51 molecules appear as a homogeneous population of small, round particles (a). Removal of the GST-tag with factor Xa results in the formation of amyloid-like fibrils and intermediate structures (b+c). After partial digestion (3 h) of GST-HD51 with trypsin, the ribbons are associated with terminal clots (d, arrow), whereas prolonged digestion (16 h) produces ribbons without attached clots (e). Removal of the GST-tag from GST-HD20 shows no evidence for the formation of defined structures (f).

FIG. 5

Birefringence of Protein Aggregates Formed by Proteolytic Cleavage of GST-HD51.

The protein aggregates were stained with Congo red. (a) Bright field, 200×; (b) Polarized light, 200X; (c) Polarized light, 100X.

FIG. 6

Polygln-Containing Protein Aggregates are Formed in vivo.

(a) Western blot analysis, after separation by 10% SDS-PAGE, of the nuclear (N) and cytosolic (C) protein fractions prepared from brain and kidney of an R6/2 hemizygous transgenic mouse and a littermate control. Blots were probed with anti-HD1, anti-GAPDH and anti-Fos B antibodies as indicated. (b) Detection of HD exon 1 protein aggregates formed in vivo using the cellulose acetate filter assay. The membrane was immunostained using the anti-HD1 antibody. (c) Ultrastructure of a neuronal intranuclear inclusion (NII). The presence of a NII in a striatal neuron of a 17 month old R6/5 homozygous mouse is shown. The NII is indicated by the large arrow and the fibrillar amyloid-like structures within the NII are indicated by two small arrows. The scale bar is 250 nm.

FIG. 7

Proposed Mechanism for the Formation of Amyloid-like Fibrils by Proteolytic Cleavage of GST-HD51

GST-HD51 molecules are represented as follows: zigzag line, elongated polygln repeat forming a stable hairpin with β-sheet structure; dotted line, N-terminal amino acids in the HD exon 1 protein containing the factor Xa cleavage site (arrow) (undefined structure); thin line, C-terminal amino acids in the HD exon 1 protein (undefined structure); shaded symbol, the dimeric globule-like form of GST.

Prior to cleavage, the HD exon 1 protein is tightly bound to the GST-tag preventing intermolecular interactions (1). Removal of the GST-tag with factor Xa renders the polygln repeat accessible allowing the formation of fibrils as seen by EM (3). During cleavage, intermediate structures form through specific polygln interactions before complete release of the GST-tag has occurred (2). These intermediates appear as clots under EM and are frequently seen at the terminals of growing fibrils.

FIG. 8

Structure of GST-HD fusion proteins (SEQ ID NOS: 38–41, respectively in order of appearance). The amino acid sequences corresponding to the N-terminal portion of huntingtin are boxed and the amino acids corresponding to the biotinylation site are underlined. Arrows labeled (Xa) and (T) indicate cleavage site for factor Xa and trypsin, respectively.

FIG. 9

Detection of polyglutamine-containing protein aggregates formed in vitro and in transfected COS-1 cells using the dot-blot filter retardation assay. (A) Purified GST-HD20DP and -HD51 DP fusion proteins (250 ng) and their factor Xa and trypsin cleavage products were applied to the filter as indicated. The aggregated proteins retained by the cellulose acetate membrane were detected by incubation with the anti-HD1 antibody. (B) Scanning electron micrograph of aggregated GST-HD51DP trypsin cleavage products retained on the surface of the cellulose acetate membrane (Photo: Heinrich Lündsdorf, GBF Braunschweig, Germany). (C) Dot-blot filter retardation assay performed on the insoluble fraction isolated from transfected and non-transfected COS-1 cells. COS-1 cells were transiently transfected with the plasmids pTL1-CAG20, -CAG51 and CAG93 encoding huntingtin exon 1 proteins with 20 (HD20), 51 (HD51) and 93 (HD93) glutamines, respectively. The pellet fractions obtained after centrifugation of whole cell lysates were subjected to DNaseI/trypsin digestion, boiled in 2% SDS, and portions of 1, 3 and 6 µl were filtered through a cellulose acetate membrane. The aggregated huntingtin protein retained on the membrane was detected with the anti-HD1 antibody. NT, non-transfected cells.

FIG. 10

Detection and quantification of aggregates formed in vitro from biotinylated GST-HD exon 1 fusion proteins. Various amounts of the fusion proteins GST-HD51DPBio and -HD20DPBio were filtered through a cellulose acetate membrane after a 3-h incubation at 37° C. in the presence or absence of trypsin as indicated. (10A) Images of the retained protein aggregates, detected with streptavidin-AP conjugate using either a fluorescent (upper panel) or a chemiluminescent AP substrate (lower panel). (10B) Quantification of signal intensities obtained for the GST-HD51DPBio dots seen in A. Fluorescence and chemiluminescence values are arbitrary units generated by the Lumi-Imager F1 and Lumi-Analyst™ software (Boehringer Mannheim).

FIG. 11

Detection (11A) and quantification (11B) of aggregates formed in vitro from biotinylated GST-HD exon 1 fusion proteins using the dot-blot and microtitre plate filter retardation assay. Various amounts of the fusion proteins GST-HD51DPBio and -HD20DPBio were filtered through the cellulose acetate membranes after a 3-h incubation at 37° C. in the presence or absence of trypsin as indicated. The detection and quantification of the aggregates was as described in FIG. 3.

FIG. 12

Detection of neurofibrillar tangles (NFTS) and β-amyloids in brain extracts prepared from Alzheimer's disease patients and controls using the dot-blot filter retardation assay. The cellulose acetate membrane was probed with the polyclonal anti-Tau, the monoclonal anti-β-amyloid, or the polyclonal anti-HD antibody. A1, A2, and A3: protein extracts prepared from cerebral cortex of Alzheimer's disease patients; C1, C2, and C3: protein extracts prepared from cerebral cortex of normal individuals. GST-HD51, fusion of glutathione S-transferase and huntingtin exon 1 containing 51 glutamines.

The examples illustrate the invention:

EXAMPLE 1

Purification of GST-HD Fusion Proteins Containing Expanded Polyglns

Exon 1 of the HD gene was isolated from genomic phage clones, derived from the normal and expanded alleles of an HD patient (Sathasivam et al., 1997), and used for the expression of GST-HD fusion proteins in *E. coli*. DNA fragments containing CAG repeats in the normal $(CAG)_{20-33}$ and expanded $(CAG)_{37-130}$ range were cloned into pGEX-5X-1 (Pharmacia), and the resulting plasmids expressing fusion proteins with 20 (GST-HD20), 30 (-HD30), 51 (-HD51), 83 (-HD83) and 122 (-HD122) glutamines, respectively, were used for protein purification. For plasmid construction lambda phage from stock $9197_4$ (Sathasivam et al., 1997) were plated to give single plaques which were inoculated into 400 ml cultures of *E. coli* XL1-Blue MRF' (Stratagene) for DNA preparation. The DNA sequence encoding the N-terminal portion of huntingtin (exon 1), including the CAG repeats, was amplified by PCR using the following pair of primers: ES 25 (TGGGATCCGCATGGCGACCCTGGAAAAGCTGATGAAGG) (SEQ ID NO: 1) corresponding to nt315-343 of the HD gene (HDCRG, 1993) and containing a BamHI site (underlined) and ES 26 (GGAGTCGACTCACGGTCGGTGCAGCGCTCCTCAGC)

(SEQ ID NO: 2) corresponding to nt516-588 and containing a SalI site (underlined). Conditions for PCR were as described (Mangiarini et al., 1996). Due to instability of the CAG repeat during propagation in E. coli, DNA preparations from individual plaques yielded different sized PCR products. Fragments of ~320, 360, 480 and 590 bp were gel-purified digested with BamHI and SalI and inserted into the BamHI-SalI site of the expression vector pGEX-5X-1 (Pharmacia), yielding pCAG30, pCAG51, pCAG83 and pCAG122, respectively, pCAG20, containing 20 repeats of CAG within the cloned HD exon 1 sequence, was similarly constructed from a phage genomic clone derived from a normal allele. All constructs were verified by sequencing. After induction with IPTG, the resulting proteins were purified under native conditions by affinity chromatography on glutathione agarose. Thus, E. coli SCS1 (Stratagene) carrying the pGEX expression plasmid of interest was grown to an $OD_{600nm}$ of 0.6 and induced with IPTG (1 mM) for 3.5 h as described in the manufacturer's protocol (Pharmacia). Cultures (200 ml) of induced bacteria were centrifuged at 4000 g for 20 min, and the resulting pellets were stored at −80° C. Cells were thawed on ice and resuspended in 5 ml of lysis buffer (50 mM sodium phosphate, 150 mM NaCl, 1 mM EDTA, pH 7.4) containing 0.5 mg/ml lysozyme. After 45 min at 0° C., cells were sonicated with two 30 sec-bursts. Octyl-β-D-glucopyranoside was then added to a final concentration of 0.1% and the resulting lysate was clarified by centrifugation at 30,000 g for 30 min at 4° C. Cleared lysates were incubated for 1 h at 4° C. with 500 µl of a 1:1 slurry of glutathione-agarose beads (Sigma) that had been washed times and resuspended in lysis buffer. The beads were poured into a small column and washed extensively with lysis buffer containing 0.1% octyl-β-D0glucopyranoside. The bound fusion protein was eluted with 2 ml of 15 mM glutathione (reduced) in lysis buffer. Typical yields were 0.5–1 mg of purified GST-HD20, -HD30 and -HD51 proteins per 200 ml of bacterial culture; yields of GST-HD83 and -HD122 were much lower, less than 10% of that obtained with the shorter fusion proteins. Protein was determined by the Bio-Rad dye binding assay using bovine serum albumin as standard. SDS-PAGE of the purified GST-HD20, -HD30, -HD51, -HD83 and -HD122 proteins revealed major bands of 42, 45, 50, 65 and 75 kDa, respectively (FIG. 1a). These bands were also detected when the various protein fractions were subjected to immunoblot analysis using the affinity purified anti-huntingtin antibody HD1 (FIG. 1b, lanes 2–6). HD1 specifically detects the GST-HD fusion proteins on immunoblots, whereas the GST-tag alone is not recognized (FIG. 1b, lane 1). For immunoblotting a bacterial plasmid encoding HD1-His, a $His_6$-tagged fusion protein containing residues 1–222 of huntingtin, was generated by inserting a PCR-amplified IT-15 cDNA fragment into the pQE-32 vector (Qiagen). The fusion protein was expressed in E. coli, affinity-purified under denaturing conditions on Ni-NTA agarose, and injected into rabbits. The resulting immune serum was then affinity-purified against the antigen that had been immobilized on Ni-NTA agarose. The GAPDH- and Fos B-specific antisera have been described (Wanker et al., 1997; Davies et al., 1997).

Western blotting was performed as detailed (Towbin et al., 1979). The blots were incubated with 1:1000 dilutions of the indicated primary antibody, followed by an alkaline-phosphatase-conjugated secondary antibody. Color development was carried out with 5-bromo-4-chloro-3-indolyl phosphate and nitroblue tetrazolium as substrates (Promega).

All recombinant proteins migrated at a size corresponding nearly to that predicted from their amino acid sequence. Interestingly, an additional high molecular weight band which remains at the top of the gel, was consistently detected in the protein fractions with the longest polyglns (83 and 122 residues; FIGS. 1a and b, lane 5 and 6). This band was most prominent on the immunoblots but was also clearly detectable in the Commassie stained gel. This immunoreactive material was often still present at the bottom of the loading slots, even after the samples had been boiled for 5 min in the presence of 2% SDS and 6 M urea prior to loading.

EXAMPLE 2

Proteolytic Cleavage of GST-HD Fusion Proteins Containing Expanded Polyglns

Figure 2:
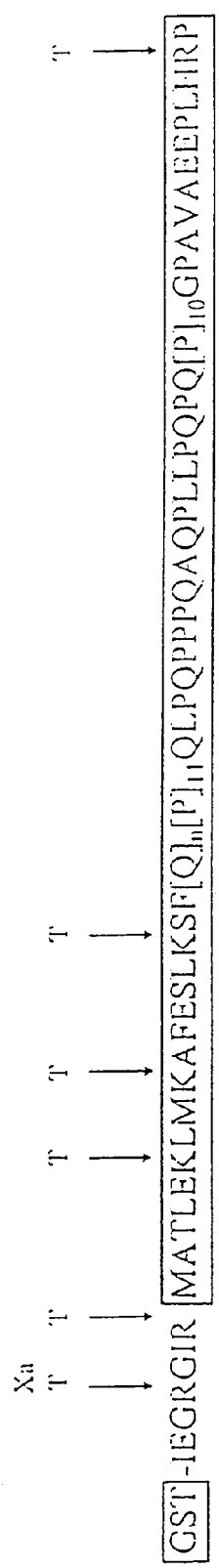

It has been shown previously that the solubility of certain proteins can be enhanced by the addition of the GST-tag (Smith and Johnson, 1988) and it was therefore of interest to determine whether the removal of the GST-tag by proteolytic cleavage would have an effect on the solubility of the polygln-containing fusion proteins. Potential factor Xa and trypsin cleavage sites within the GST-HD fusion proteins are shown in FIG. 2. Factor Xa cleaves between the GST-tag and the HD exon 1 protein whereas trypsin removes an additional 15 amino acids from the N-terminus and a single proline from the C-terminus, both proteases leaving the polygln repeat intact. The GST-HD20, -HD30 and -HD51 proteins were digested with trypsin under conditions designed to remove the GST-tag from the fusion protein without it being totally degraded. After cleavage, proteins were denatured by boiling in the presence of 2% SDS and analyzed by SDS-PAGE and immunoblotting using the anti-HD1 antibody. GST-HD20 and -HD30 cleavage yielded products migrating in a 12:5% gel at approximately 30 and 33 kDa, respectively. In contrast, cleavage of GST-HD51 resulted in the formation of two protein products migrating at approximately 37 and 60 kDa, and an additional weak immunoreactive band on the bottom of the loading slots was also detected (FIG. 3a). This high molecular weight band was more pronounced when GST-HD51 was digested with trypsin under conditions in which the GST-tag was totally degraded (FIG. 3b). However, with proteins GST-HD20 and -HD30 this longer exposure to trypsin produced the same cleavage products as the ones seen in FIG. 3a and the high molecular weight products were not observed. Similar results were obtained with factor Xa protease and endoproteinases Arg-C and Lys-C. As regards the proteolytic cleavages, the following protocols were carried out: The GST-HD fusion proteins purified as described above were dialysed against 40 mM Tris-HCl (pH 8.0), 150 mM NaCl, 0.1 mM EDTA and 5% (v/v) glycerol to raise the pH prior to proteolytic cleavage. The proteins were then combined with bovine factor Xa (New England Biolabs) or modified trypsin (Boehringer Mannheim, sequencing grade) in dialysis buffer containing 2 mM $CaCl_2$ at an enzyme:substrate ratio of 1:10 (w/w) or 1:40 (w/w), respectively. Incubations with factor Xa were at 25° C. for 16 h. Tryptic digestions were performed at 37° C. for 3 or 16 h as indicated. Digestions were terminated by the addition of PMSF to 1 mM. The degree of proteolysis was determined by SDS-PAGE followed by staining with Coomassie blue or immunoblottting using anti-HD1 antibody.

We have developed a simple and sensitive filter assay to detect the formation of high molecular weight insoluble protein aggregates. This assay is based on the finding that the SDS-insoluble protein aggregates obtained by proteolytic cleavage of GST-HD51 are retained on a cellulose acetate filter, whereas the soluble cleavage products of GST-HD20 and GST-HD30 are not. Factor Xa or trypsin digestions of purified GST-HD fusion proteins (10 µg) were performed in a 20 µl reaction mixture as described above. Reactions were terminated by adjusting the mixture to 2% SDS and 50 mM DTT. After heating at 100° C. for 5 min, aliqouts (0.5 µl) were diluted into 200 µl of 0.1% SDS and filtered through a cellulose acetate membrane (Schleicher & Schuell, 0.2 µm pore size) using a BRL dot blot filtration unit. Filters were washed with water, and the SDS-insoluble aggregates retained on the filter detected by incubation with the anti-HD1 antibody, followed by an anti-rabbit secondary antibody conjugated to alkaline phosphatase (Boehringer Mannheim). FIG. 3c shows immunoblots of cellulose acetate and nitrocellulose membranes to which the native GST-HD20, -HD30 and -HD51 proteins and their factor Xa and trypsin cleavage products have been applied. On the cellulose acetate filter, only the cleavage products of GST-HD51 were detected by the anti-HD1 antibody, indicating the formation of insoluble high molecular weight protein aggregates. In contrast, all the uncleaved GST-HD fusion proteins and their digestion products were detected on the nitrocellulose control filter. This assay was also used to detect huntingtin aggregates present in a nuclear fraction from the brain of an R6/2 hemizygous mouse and littermate control (see preparation of nuclei below).

EXAMPLE 3

Huntingtin Proteins Containing Expanded PolyGlns in the Pathological Range Aggregate to Amyloid-Like Birefringent Fibrils Electron microscopy of negatively stained GST-HD51 fractions showed oligomeric particles with diameters of 6 to 7 nm (FIG. 4a); no higher ordered aggregates were observed. For electron microscopic observation, the native or protease-digested GST-HD fusion proteins were adjusted to a final concentration of 50 µg/ml in 40 mM Tris-HCl (pH 8.0), 150 mM NaCl, 0.1 mM EDTA and 5% glycerol. Samples were negatively stained with 1% uranyl acetate and viewed in a Philips CM100 EM. In contrast, protein fractions obtained by proteolytic cleavage of GST-HD51 showed numerous clusters of high molecular weight fibrils and ribbon-like structures (FIGS. 4b, c, d and e), reminiscent of purified amyloids (Prusiner et al., 1983). The fibrils obtained after digestion with factor Xa showed a diameter of 10–12 nm and their length varied from 100 nm up to several micrometers (FIGS. 4b and c). In the trypsin-treated samples ribbon-like structures formed by lateral aggregation of fibrils with a diameter of 7.7 nm were observed (FIGS. 4d and e). After treatment with factor Xa or limited digestion with trypsin, clots of small particles were frequently detected on one or both ends of the fibrils (FIGS. 4b, c and d). These clots of varying sizes and shapes were not seen when GST-HD51 was digested with trypsin under conditions in which the GST-tag is totally degraded (FIG. 4e), indicating that they contain GST. In strong contrast to GST-HD51, the GST-HD20 and -HD30 proteins did not show any tendency to form ordered high molecular weight structures, either with or without protease treatment (FIG. 4f).

Figure 5:
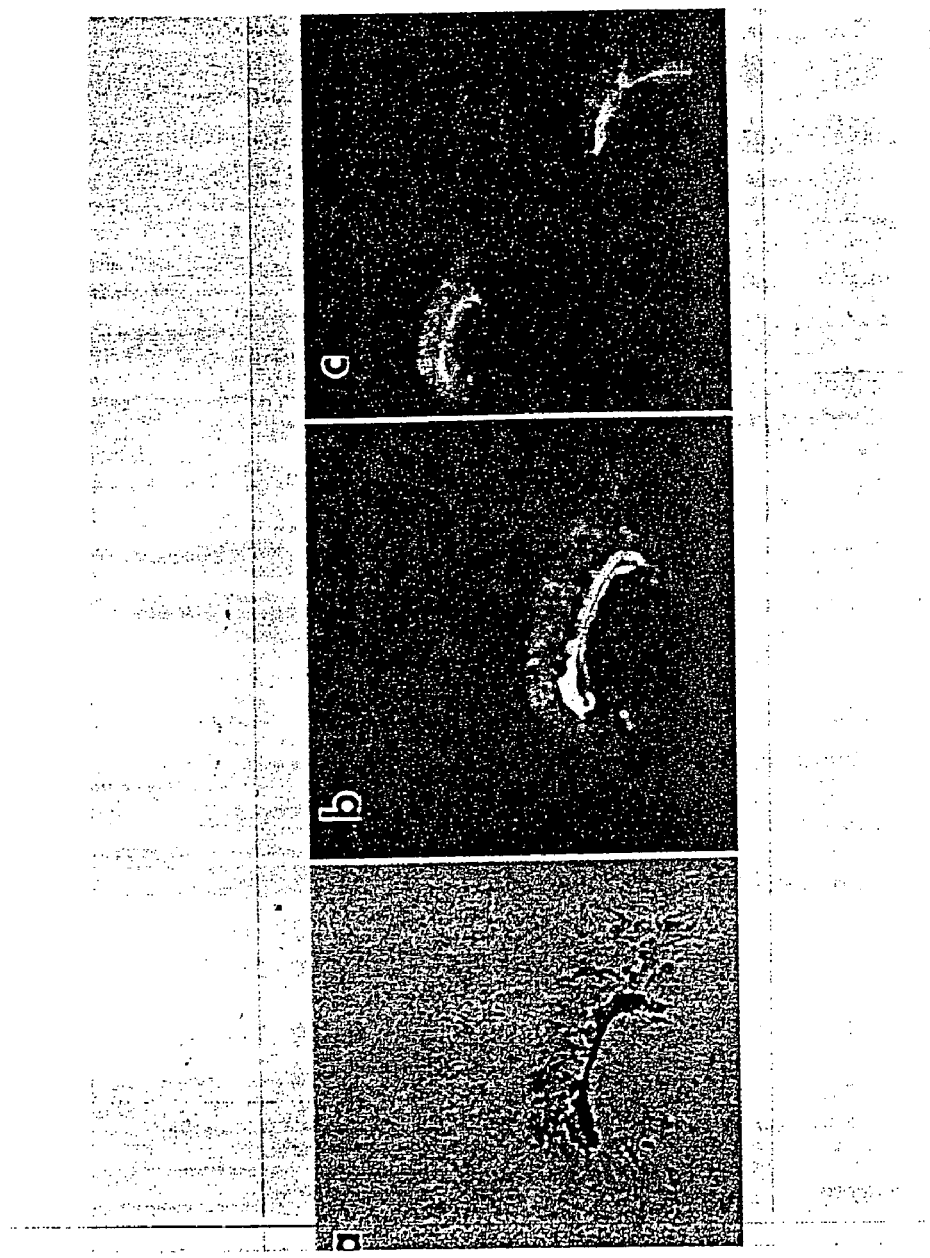

The insoluble protein aggregates formed by proteolytic cleavage of GST-HD51 were isolated by centrifugation and stained with Congo red (Caputo et al., 1992) and examined under a light microscope. For light microscopy, peptide aggregates formed by trypsin digestion of purified GST-HD fusion proteins (50 µg in 100 µl of digestion buffer) were collected by centrifugation at 30,000 g for 1 h and resuspended in 10 µl of water. Samples were mixed with 0.1 volume of a 2% (w/v) aqueous Congo Red (Sigma) solution, placed on aminoalkylsilane-coated glass slides, and allowed to dry overnight under a coverslip. After removing the coverslip, excess Congo Red was removed by washing with 90% ethanol. Evaluation of the Congo Red staining by polarization microscopy was performed using a Zeiss Axiolab Pol microscope equipped with strain-free lenses and optimally aligned cross-polarizers. After staining, the protein aggregates on the glass slides were red, indicating that they had bound the dye (FIG. 5a), and when examined under polarized light a green color and birefringence were detected (FIGS. 5b and c). These staining characteristics were similar to those observed for prions (Prusiner et al., 1983) and amyloids (Caputo et al., 1992).

EXAMPLE 4

Figure 6:
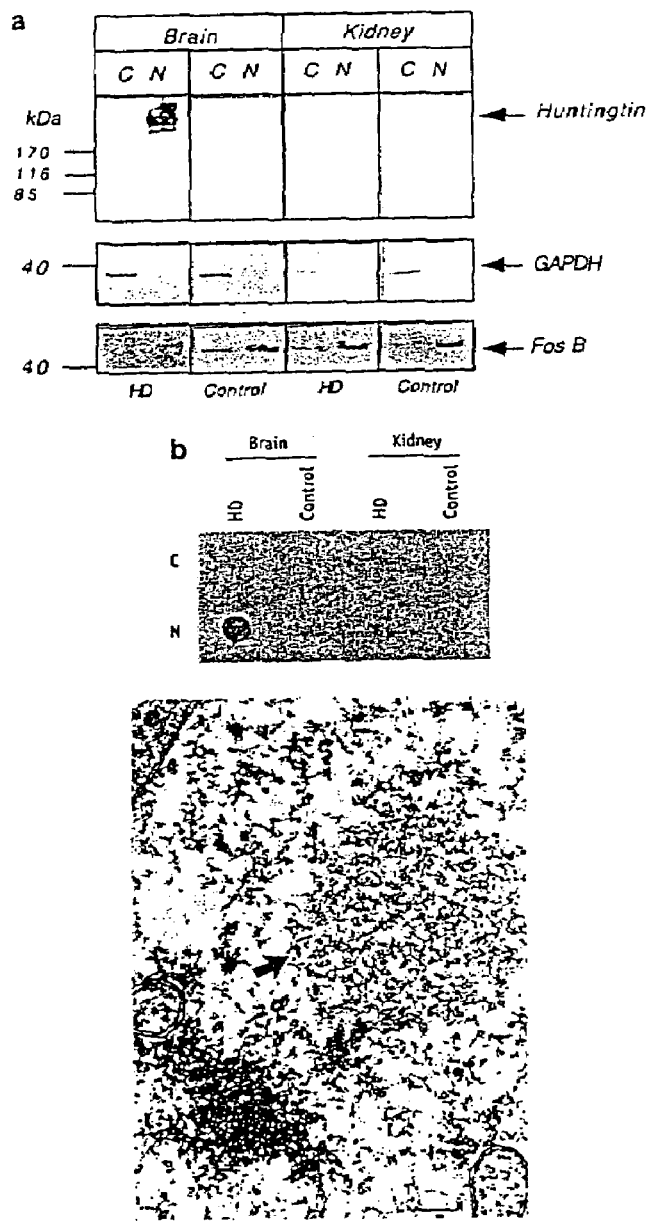

Huntingtin Proteins Containing Expanded PolyGlns Form Amyloid-Like Protein Aggregates In Vivo To determine whether the amyloid-like protein aggregates formed by proteolytic cleavage of GST-HD51 in vitro are also present in vivo, nuclear protein fractions of brain and kidney were prepared from mice transgenic for the HD mutation (line R6/2) and littermate controls (Davies et al., 1997; Mangiarini et al., 1996). Nuclei from the brain or kidney of an R6/2 hemizygous mouse with a repeat expansion of $(CAG)_{143}$ (Mangiarini et al., 1996) at ten weeks of age and littermate control were prepared as follows. Whole brain samples (80 mg) in 400 ml of 0.25 M sucrose in buffer A (50 mM triethanolamine [pH 7.5], 25 mM KCl, 5 mM $MgCl_2$, 0.5 mM DTT, 0.5 mM PMSF) were homogenized using 15 strokes of a tight-fitting glass homogenizer. The homogenate was adjusted to a final concentration of 5 mM DTT, and centrifuged at 800 g for 15 min. The supernatant was recentrifuged at 100,000 g for 1 h, and the supernatant from this centrifugation was taken as the cytosolic fraction (fraction C). The loose pellet from the first centrifugation was homogenized, diluted to 1.2 ml with 0.25 M sucrose/buffer A, and mixed with two volumes of 2.3 M sucrose/buffer A. The mixture was then layered on top of 0.6 ml 2.3 M sucrose/bufferA in a SW60 tube and centrifuged at 124,000 g for 1 h. The pellet was harvested with a spatula, resuspended in 200 µl of 0.25 M sucrose/buffer A and again centrifuged at 800 g for 15 min. The entire procedure was carried out at 4° C. The pelleted nuclei were resuspended to a density of $\sim 1 \times 10^7$ nuclei/ml in 0.25 sucrose/buffer A (fraction N) and stored at −80° C. Nuclei from mouse kidney were prepared in the same way. The protein extracts were analyzed by SDS-PAGE and Western blotting using the anti-HD1 antibody (FIG. 6a). Strikingly, this antibody detected a prominent high molecular weight band in the nuclear fraction (N) prepared from R6/2 transgenic brain, very similar to the high molecular weight band obtained by proteolytic cleavage of GST-HD51 (FIG. 3b). No such immunoreactive band was detected in the nuclear fraction of brain from the littermate control and it was also absent from the corresponding cytoplasmic fractions (C). A small amount of high molecular weight material was also detected in the nuclear fraction prepared from R6/2 transgenic kidney, but was again absent from the cytoplasmic fraction. The purity of the nuclear and cytoplasmic fractions was confirmed by Western blot analysis using the anti-Fos B and anti-GAPDH antibodies. Anti-Fos B detected the transcription factor mainly in the nuclear fraction, and the enzyme GAPDH was only seen in the cytoplasmic fraction, as expected. The Western blot results were reproduced using the cellulose acetate filter assay (FIG. 6b). Using this assay, a 10–20 fold higher amount of transgene protein was detected in the nuclear fraction isolated from brain material, compared to that prepared from kidney.

The formation of NIIs has been shown to preceed the neuronal dysfunction that forms the basis of the progressive neurological phenotype observed in the R6 transgenic lines (Davies et al., 1997). These NIIs are immunoreactive for both huntingtin and ubiquitin antibodies and contain the transgene but not the endogenous huntingtin protein. Therefore, Western blot analysis using an anti-ubiquitin antibody was also performed showing the same pattern of immunoreactivity as had been observed with the anti-HD1 antibody (FIG. 6a), and indicating that the high molecular weight transgene protein present in the nuclear fraction is ubiquitinated (data not shown).

To examine whether the NIIs containing the proteins huntingtin and ubiquitin (Davies et al., 1997) have a fibrous composition, an ultrastructural analysis was performed. Experimentally, a 17 month old R6/5 homozygous mouse ((CAG)$_{128-155}$) (Mangiarini et al., 1996) was deeply anaesthetised with sodium pentobarbitone and then perfused through the left cardiac ventricle with 35–50 ml of 4% paraformaldehyde and either 0.5% glutaraldehyde in 0.1 M Millonig's phosphate buffer (pH 7.4). The brain was removed from the skull and placed in fresh fixative overnight at 4° C. Coronal sections (50–200 μm) were cut on an Oxford Vibratome (Lancer) and collected in serial order in 0.1 M phosphate buffer. After being osmicated (30 min in 1% OsO$_4$ in 0.1 M phosphate buffer) the sections were stained for 15 min in 0.1% uranyl acetate in sodium acetate buffer at 4° C., dehydrate in ethanols, cleared in propylene oxide and embedded in Araldite between two sheets of Melanex (ICI). Semi thin (1 μm) sections were cut with glass knife on a Reichert Ultracut ultramicrotome. The sections were collected on mesh grids coated with a thin formvar film, counterstained with lead citrate and viewed in a Jeol 1010 electron microscope. An electron micrograph of a NII from a 17 month old R6/5 homozygous mouse is shown in FIG. 6c. This NII (large arrow) contains high molecular weight fibrous structures which were clearly differentiated from the surrounding chromatin. The filaments were randomly oriented, 5–10 nm in diameter and often measured up to 250 nm in length (small arrows). These structures differ from those previously reported in the NIIs seen in hemizygous R6/2 mice which were far more granular in composition, with individual filamentous structures being more difficult to distinguish (Davies et al., 1997). R6/2 mice exhibit an earlier age of onset with a more rapid progression of the phenotype and do not survive beyond 13 weeks (Mangiarini et al., 1996). It is possible that the filamentous structures do not have time to form in the R6/2 mice.

EXAMPLE 5

Construction of Further Plasmids, Purification of Corresponding GST Fusion Proteins and Proleolytic Cleavage of GST Fusion Proteins In a second set of experiments, a further number of plasmids was constructed. Standard protocols for DNA manipulations were followed (J. Sambrook, E. F. Fritsch, and T. Maniatis, Molecular Cloning: A Laboratory Manual, 2nd Ed., Cold Spring Harbor Laboratory Press, Plainview, N.Y., 1989). IT-15 cDNA sequences (HDCRG, Cell 72, 971 (1993)) encoding the N-terminal portion of huntingtin, including the CAG repeats, were amplified by PCR using the oligonucleotides ES25 (5'-TGGGATCCGCATGGCGAC-CCTGGAAAAGCTGATGA AGG-3') (SEQ ID NO: 1) and ES27 (3'-CTCCTCGAGCGGCGGTGGCGGC TGTTGCT-GCTGCTGCTG-5') (SEQ ID NO: 3) as primers and the plasmids pCAG20 and pCAG51 as template (E. Scherzinger, R. Lurz, M. Trumaine, L. Margiarini, B. Hollenbach, R. Hasenbank, G. P. Bates, S. W. Davies, H. Lehrach, and E. E. Wanker, Cell 90, 549 (1997)). Conditions for PCR were as described (L. Mangiarini, K. Sathasivam, M. Seller, B. Cozens, A Harper, C. Hetherington, M. Lawton, Y Trottier, H. Lehrach, S. W. Davies, and G. P. Gates, Cell 87, 493 (1996)). The resulting cDNA fragments were gel purified, digested with Bam HI and Xho I and were inserted into the Bam HI-Xho I site of the expression vector pGEX-5X-1 (Pharmacia), yielding pCAG20DP and pCAG51DP, respectively. The plasmids pCAG20DP-Bio and pCAG51DP-Bio were generated by subcloning the PCR fragments obtained from the plasmids pCAG20 and pCAG51 into pGEX-5X-1-Bio. PGEX-5X-1-Bio was created by ligation of the oligonucleotides BIO1 (5'-CGCTCGAGGGTATCTTC-GAGGCCCAGAAGATCGAGTG GCGATCACCATGAG-3') (SEQ ID NO: 4) and BIO2 (5'-GGCCGCTCATG GTGATCGCCACTCGATCTTCTGGGCCTC-GAAGATACCCTCGAG-3') (SEQ ID NO: 5), after annealing and digestion with Xho I, into the Xho I-Not I site of pGEX-5X-1. The plasmids with the IT-15 cDNA inserts were sequenced to confirm that no errors had been introduced by PCR. The construction of plasmids pTL1-CAG20, pTL1-CAG51 and pTL1-CAG93 for the expression of huntingtin exon 1 proteins containing 20, 51 and 93 glutamines in mammalian cells has been described (A. Sittler, S. Walter, N. Wedemeyer, R. Hasenbank, E. Scherzinger, G. P. Bates, H. Lehrach, and E. E. Wanker, Mol. Cell, submitted).

Figure 8:
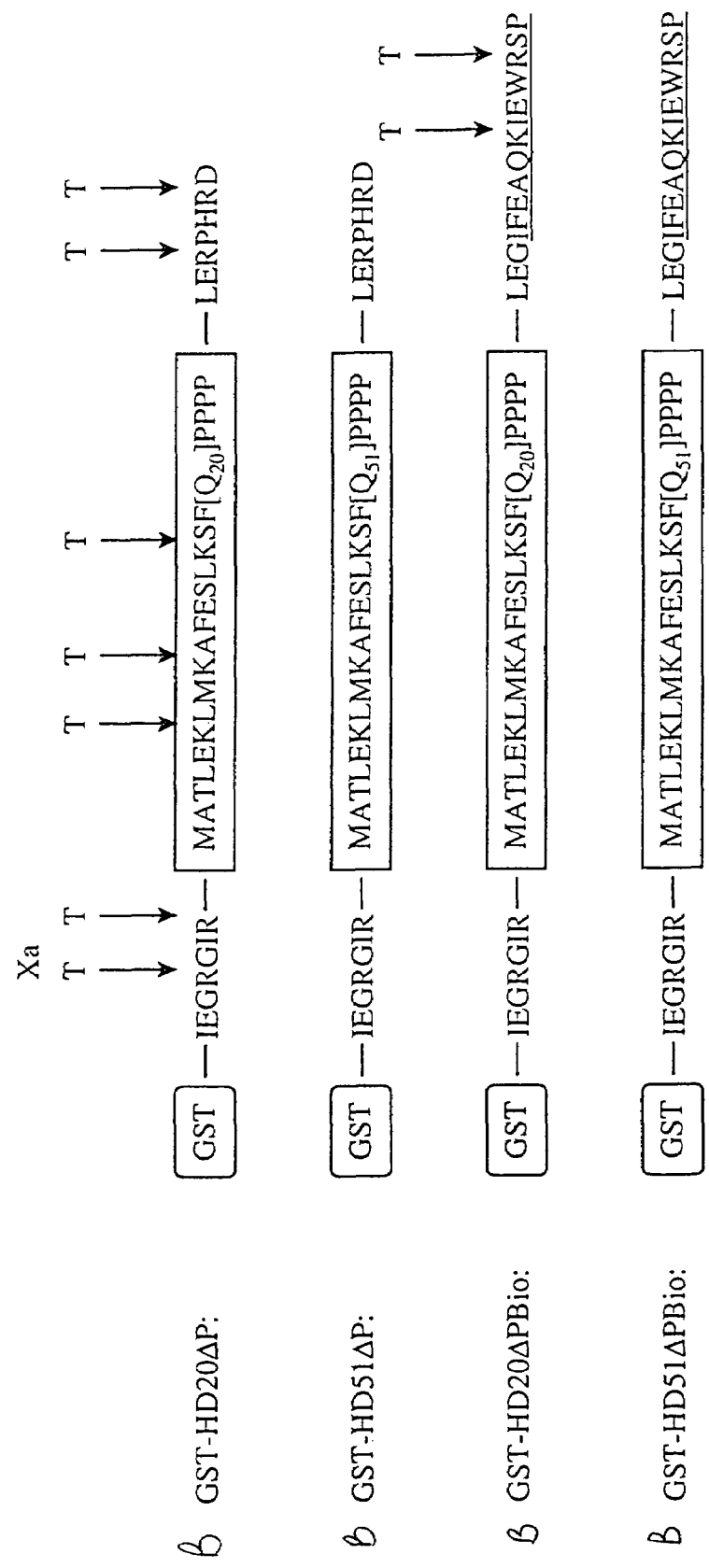

The amino acid sequence of the GST-HD fusion proteins encoded by the E. coli expression plasmids pCAG20DP, pCAG51DP, pCAG20Dp-Bio and pCAG51DP-Bio is shown in FIG. 8. The plasmids pCAG20DP and pCAG51DP encode fusion proteins of glutathione S-transferase (GST) and the N-terminal portion of huntingtin containing 20 (GST-HD20DP) and 51 (-HD51DP) polyglutamines, respectively. In these proteins the proline-rich region located immediately downstream of the glutamine repeat was deleted (E. Scherzinger, R. Lurz, M. Trumaine, L. Margiarini, B. Hollenbach, R. Hasenbank, G. P. Bates, S. W. Davies, H. Lehrach, and E. E. Wanker, Cell 90, 549 (1997). The fusion proteins GST-HD20DPBio and -HD51DPBio are identical to GST-HD20DP and -HD51DP, except for the presence of a biotinylation site (P. J. Schatz, Biotechnology 11, 1138 (1993)) at their C-termini.

In the experiments described herein, E. coli DH10B (BRL) was used for plasmid construction and E. coli SCS1 (Stratagene) was used for the expression of GST-HD fusion proteins. Transformation of E. coli with plasmids and ligation mixtures was performed by electroporation using a Bio-Rad Gene Pulser (Richmond, Calif.). Transformed cells were spread on LB plates supplemented with appropriate antibiotics (J. Sambrook, E. F. Fritsch, and T. Maniatis, Molecular Cloning: A Laboratory Manual, 2nd Ed., Cold Spring Harbor Laboratory Press, Plainview, N.Y. 1989). For expression of GST fusion proteins, cells were grown in liquid TY medium (5 g NaCl, 5 g yeast extract, and 10 g tryptone per liter) buffered with 20 mM MOPS/KOH (pH 7.9) and supplemented with glucose (0.2%), thiamine (20 µg/ml), ampicillin (100 µg/ml) and kanamycin (25 µg/ml).

The procedure for purification of GST fusion proteins is an adaption of the protocol of Smith and Johnson (D. B. Smith and K. S. Johnson, *Gene* 67, 31 (1988)). Unless indicated otherwise, all steps were performed at 0–4° C.

First, 100 ml TY medium were inoculated with a single colony containing the expression plasmid of interest, and the culture was incubated at 37° C. overnight with shaking. Then, 1.5 liter TY medium were inoculated with the overnight culture and grown at 37° C. until an $OD_{600}$ of 0.6 was reached. IPTG was added to a final concentration of 1 mM, and the culture continued to grow at 37° C. for 3.5 h with vigorous shaking. The culture was chilled on ice, and the cells harvested by centrifugation at 4000× g for 20 min.

Cells were washed with buffer A [50 mM sodium phosphate (pH 8), 150 mM NaCl, and 1 mM EDTA]. If neccessary, the cell pellet was stored at −70° C. Cells were resuspended in 25 ml buffer A. PMSF and lysozyme (Boehringer Mannheim) were added to 1 mM and 0.5 mg/ml, respectively, and incubated on ice for 45 min. Cells were lysed by sonication (2×45 s, 1 min cooling, 200–300 Watt), and Triton X-100 was added to a final concentration of 0.1% (v/v). The lysate was centrifuged at 30.000× g for 30 min, and the supernatant was collected.

5 ml of a 1:1 slurry of GST-agarose (Sigma), previously equilibrated in buffer A, was added and the mixture was stirred for 30 min. The slurry was poured into a 1.6 cm diameter column, washed once with 40 ml buffer A containing 1 mM PMSF and 0.1% Triton X-100 and twice with 40 ml buffer A containing 1 mM PMSF. The protein was eluted with 5×2 ml buffer A containing 15 mM reduced glutathione (Sigma). Aliquots of the fractions were analyzed by SDS-PAGE and the fractions containing purified GST fusion protein were combined. Finally, the pooled fractions were dialysed overnight against buffer B [20 mM Tris/HCl (pH 8), 150 mM NaCl, 0.1 mM EDTA and 5% (v/v) glycerol], aliquotted, freezed in liquid nitrogen and stored at −70° C.

Typical yields were 10–20 mg for GST-HD20DP and -HD51DP and 5–10 mg for GST-HD20DPBio and -HD51DPBio per liter of bacterial culture. Protein concentration was determined using the Coomassie protein assay reagent from Pierce with BSA as a standard.

The GST-huntingtin fusion proteins (2 mg) were digested with bovine factor Xa (New England Biolabs) or with modified trypsin (Boehringer Mannheim, sequencing grade) at an enzyme/substrate ratio of 1:10 (w/w) and 1:20 (w/w), respectively. The reaction was carried out in 20 µl of 20 mM Tris/HCl (pH 8), 150 mM NaCl and 2 mM $CaCl_2$. Incubations with factor Xa were performed at 25° C. for 16 h. Tryptic digestions were at 37° C. for 3 to 16 h. Digestions were terminated by the addition of 20 µl 4% (w/v) SDS and 100 mM DTT, followed by heating at 98° C. for 5 min.

Figure 9:
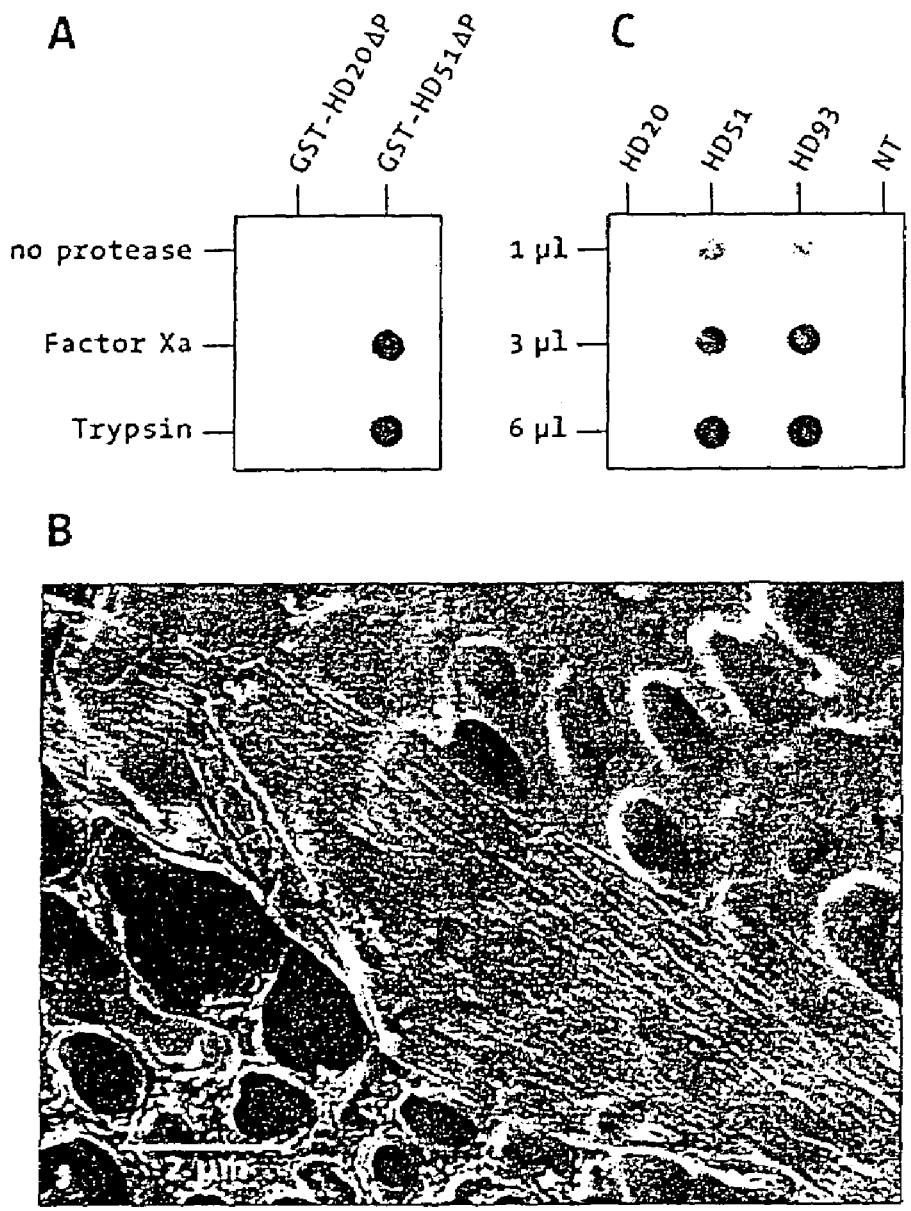

As shown in the previous examples, removal of the GST tag from the HD exon 1 protein containing 51 glutamines (GST-HD51) by site-specific proteolytic cleavage results in the formation of high molecular weight protein aggregates, seen as characteristic fibrils or filaments on electron microscopic examination. Such ordered fibrillar structures were not detected after proteolysis of fusion proteins containing only 20 (GST-HD20) or 30 (GST-HD30) glutamines, although light scattering measurements (Y. Georgalis, E. B. Starikov, B. Hollenbach, R. Lurz, E. Scherzinger, W. Saenger, H. Lehrach, and E. E. Wanker, *Proc. Natl. Acad. Sci. USA* 95, 6118 (1998)) revealed that some form of aggregation also occured with these normal repeat-length proteins. In the present example, truncated GST-HD exon 1 fusion proteins with or without a C-terminal biotinylation tag (P. J. Schatz, *Biotechnology* 11, 1138 (1993)) were used. These fusion proteins contain either 20 or 51 glutamines but lack most of the proline rich region located downstream of the glutamine repeat (E. Scherzinger, R. Lurz, M. Trumaine, L. Margiarini, B. Hollenbach, R. Hasenbank, G. P. Bates, S. W. Davies, H. Lehrach, and E. E. Wanker, *Cell* 90, 549 (1997)). Potential factor Xa and trypsin cleavage sites within the GST-HD fusion proteins are shown in FIG. 8. As outlined above, the proteins GST-HD20DP and -HD51DP were expressed in *E. coli* and affinity-purified under native conditions. They were then digested overnight with trypsin or faxtor Xa protease to promote the formation of polyglutamine-containing huntingtin aggregates. FIG. 9A shows an immunoblot of a cellulose acetate membrane to which the native GST-HD20DP and -HD51DP proteins and their factor Xa and trypsin cleavage products have been applied.

Figure 10:
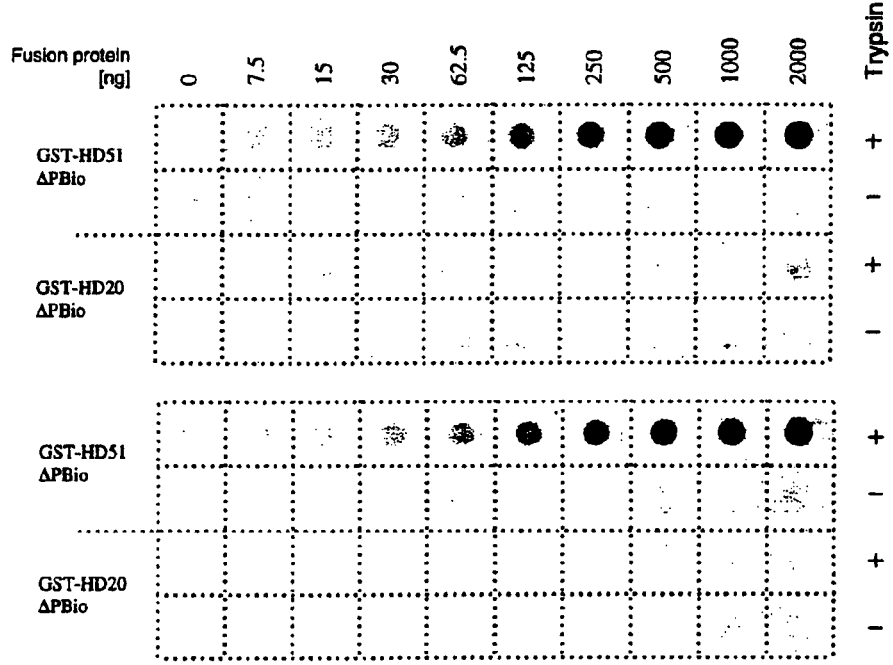
Figure 10:
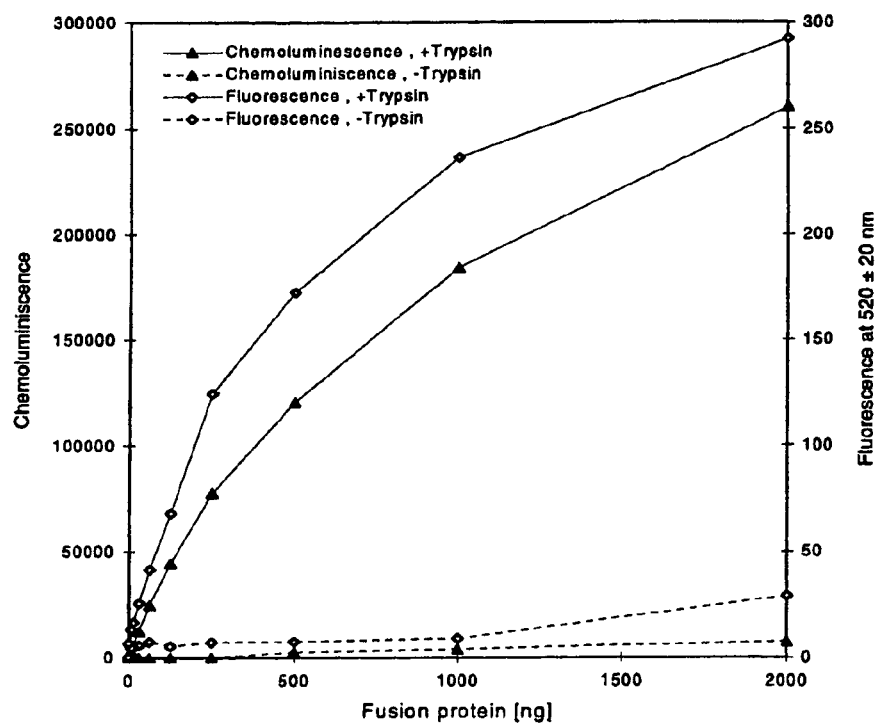

To monitor the in vitro formation of polyglutamine-containing aggregates without the need for a specific antibody, a modified filter retardation assay was developed. In this assay, streptavidin-conjugated alkaline phosphatase (AP) is used to detect the insoluble protein aggregates retained on the cellulose acetate filter membrane. Streptavidin binds specifically to the biotinylation tag (P. J. Schatz, *Biotechnology* 11, 1138 (1993)) that has been added C-terminal to the polyglutamine tract in the fusion proteins GST-HD20DPBio and -HD51DPBio (FIG. 7) (see Example 8 for details). FIG. 10A shows that the modified aggregation assay gives results comparable to those obtained with the non-biotinylated fusion proteins in that insoluble aggregates are produced from the trypsin-treated GST-HD51DPBio protein but not from the uncleaved GST-HD51DPBio protein or the corresponding 20 repeat samples. Using either fluorescent (AttoPhos™) or chemiluminescent (CDP-Star™) substrates for alkaline phosphatase, it is possible to capture and quantify the filter assay results with the Boehringer Lumi-Imager F1 system. With both AP substrates, aggregates formed from as little as 5–10 ng of input GST-HD51DPBio protein were readily detected on the cellulose acetate membrane, and signal intensities increased linearly up to 250 ng of fusion protein applied to the filter (FIG. 10B).

EXAMPLE 6

Isolation of Amyloid-Like Protein Aggregates from Transfected COS-1 Cells

To examine whether polyglutamine-containing aggregates are also formed in vivo, HD exon 1 proteins with 20, 51 or 93 glutamines (without a GST tag) were expressed in COS-1 cells. Whole cell lysates were prepared, and after centrifugation, the insoluble material was collected and treated with DNaseI and trypsin to lower the viscosity. The resulting protein mixture was then boiled in SDS and analyzed using the dot-blot filter retardation assay (see Example 8). In more detail, the following experimental protocol was carried out:

COS-1 cells were grown in Dulbecco's modified Eagle medium (Gibco BRL) supplemented with 5% (w/v) fetal calf serum (FCS) containing penicillin (5 U/ml) and streptomycin (5 µg/ml), and transfection was performed as described (A. Sittler, D. Devys, C. Weber, and J.-L. Mandel, *Hum. Mol. Genet.* 5, 95 (1996)).

COS-1 cells transfected with the mammalian expression plasmids pTL1-CAG20, pTL1-CAG51 and pTL1-CAG93 were harvested 48 h after transfection. The cells were washed in ice cold PBS, scraped and pelleted by centrifugation (2000× g, 10 min, 4° C.). Cells were lysed on ice for 30 min in 500 ml lysis buffer [50 mM Tris/HCl (pH 8.8), 100 mM NaCl, 5 mM $MgCl_2$, 0.5% (w/v) NP-40, 1 mM EDTA] containing the protease inhibitors PMSF (2 mM), leupeptin (10 μl/ml), pepstatin (10 μg/ml), aprotinin (1 μg/ml) and antipain (50 μg/ml). Insoluble material was removed by centrifugation for 5 min at 14000 rpm in a microfuge at 4° C. Pellets containing the insoluble material were resuspended in 100 ml DNase buffer [20 mM Tris/HCl (pH 8.0), 15 mM $MgCl_2$], and DNase I (Boehringer Mannheim) was added to a final concentration of 0.5 mg/ml followed by incubation at 37° C. for 1 h. After DNase treatment the protein concentration was determined by the Dot Metric assay (Geno Technology) using BSA as a standard. Eight μl 1 M Tris/HCl (pH 8.4), 1 μl 1% (w/v) SDS, 1 μl 0.2 M $CaCl_2$ and 10 μl trypsin (0.25 mg/ml) were then added, and the mixture was incubated for an additional 4 h at 37° C. Digestions were terminated by adjusting the mixtures to 20 mM EDTA, 2% (w/v) SDS and 50 mM DTT, followed by heating at 98° C. for 5 min.

FIG. 9C shows that insoluble protein aggregates are being formed in transfected COS cells expressing the HD exon 1 protein with 51 and 93 glutamines but not in COS cells expressing the normal exon 1 allele with 20 glutamines or in the non-transfected control cells. Thus, as observed in vitro with purified GST fusion proteins, formation of high molecular weight protein aggregates in vivo occurs in a repeat length-dependent way and requires a polyglutamine repeat in the pathological range. In addition, like the in vitro aggregates, the HD exon 1 aggregates formed in vivo are resistant to digestion with trypsin as well as to boiling in 2% (w/v) SDS.

EXAMPLE 7

Isolation of Amyloid-Like Protein Aggregates from Alzheimer's Disease Brain

It has been shown that the neurodegenerative-disorder Alzheimer's disease (AD) is caused by the the formation of β-amyloids and neurofibrillar tangles (NFTs) mainly occuring in the neocortex, hippocampus and amygdala (K. Beyreuther, and C. L. Masters, *Nature* 383, 476 (1996)). To determine whether these structures can be detected by the dot-blot filter retardation assay brain extracts of patients and controls were prepared and analyzed using the anti-Tau, anti-β-amyloid and anti-HD1 antibodies.

Figure 12:
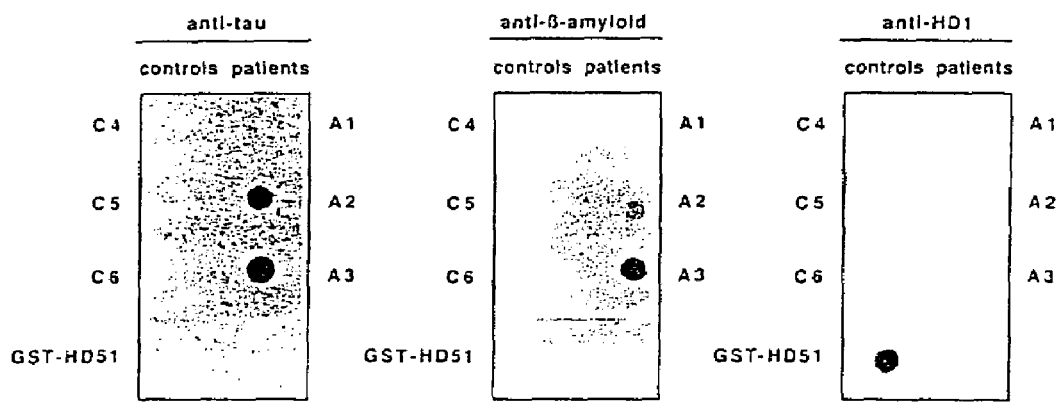

FIG. 12 shows that with the anti-Tau and anti-β-amyloid antibodies NFTs and β-amyloids were detected in brain extracts prepared from patients A2 and A3, but not in brain extracts prepared from patient A1 and the controls. Clinical studies revealed that the patients A2 and A3 had Alzheimer's disease with an intermediate and severe intellectual impairment, respectively, whereas patient A1 suffered only from moderate intellectual impairment. This indicates that the results obtained with the filter retardation assay correlate with the severity of the disease. Using the HD1 antibody in the brain extracts prepared from AD patients and controls no aggregated huntingtin protein was detected. However, the antibody reacted with the GST-HD51 protein which was used as a positive control.

Human cerebral cortex (~500 mg) was homogenized in 2.5 ml of lysis buffer (0.32 M sucrose, 1 mM $MgCl_2$, 5 mM $KH_2PO_4$, pH 7.0, 1 mM PMSF) using nine strokes of a glass homogenizer. The homogenat was centrifuged for 15 min at 500×g to remove the nuclei. The original supernatant was then centrifuged at 93500×g for 1 h yielding a membrane pellet. The pellet was dissolved in 2–5 ml 100 mM Tris-HCl (pH 8), 0.5% SDS and trypsin (Boehringer Mannheim, sequencing grade) was added to a final concentation of 0.05 mg/ml followed by incubation at 37° C. overnight. Digestions were terminated by adjusting the mixtures to 2% SDS and 50 mM DTT, followed by heating at 98° C. for 5 min. The mixture was centrifuged for 1 h at 110000×g and the resulting pellet was resuspended in 100 μl of water. Aliquots (2–10 μl) were then used for the analysis with the dot-blot filter retardation assay.

EXAMPLE 8

Dot-Blot Filter Retardation Assay

The filter assay used to detect polyglutamine-containing huntingtin protein aggregates has been described (hereinabove and in E. Scherzinger, R. Lurz, M. Trumaine, L. Margiarini, B. Hollenbach, R. Hasenbank, G. P. Bates, S. W. Davies, H. Lehrach, and E. E. Wanker, *Cell* 90, 549 (1997)). Denatured and reduced protein samples were prepared as described above, and aliquots corresponding to 50–250 ng fusion protein (GST-HD20DP and GST-HD51 DP) or 5–30 μg extract protein (pellet fraction) were diluted into 200 μl 0.1% SDS and filtered on a BRL dot blot filtration unit through a cellulose acetate membrane (Schleicher and Schuell, 0.2 μm pore size) that had been preequilibrated with 0.1% SDS. Filters were washed 2 times with 200 μl 0.1% SDS and were then blocked in TBS (100 mM Tris/HCl, pH 7.4, 150 mM NaCl) containing 3% nonfat dried milk, followed by incubation with the anti-HD1 (1:1000) (see above and E. Scherzinger, R. Lurz, M. Trumaine, L. Margiarini, B. Hollenbach, R. Hasenbank, G. P. Bates, S. W. Davies, H. Lehrach, and E. E. Wanker, *Cell* 90, 549 (1997), the anti-Tau (Dako, 1:1000) or the anti-β-amyloid antibody (Dako, 1:300). The filters were washed several times in TBS, then incubated with a secondary anti-rabbit or anti-mouse antibody conjugated to horse raddish peroxidase (Sigma, 1:5000) followed by ECL (Amersham) detection. The developed blots were exposed for various times to Kodak X-OMAT film or to a Lumi-imager (Boehringer Mannheim) to enable quantification of the immunoblots. For detection and quantification of polyglutamine-containing aggregates generated from the protease-treated fusion proteins GST-HD20DPBio and -HD51DPBio, the biotin/streptavidin-AP detection system was used. Following filtration, the cellulose acetate membranes were incubated with 1% (w/v) BSA in TBS for 1 h at room temperature with gentle agitation on a reciprocal shaker. Membranes were then incubated for 30 min with streptavidin-alkaline phosphatase (Promega) at a 1:1000 dilution in TBS containing 1% BSA, washed 3 times in TBS containing 0.1% (v/v) Tween 20 and 3 times in BSA, and finally incubated for 3 min with either the fluorescent alkaline phosphatase substrate AttoPhos™ or the chlorosubstituted 1,2-dioxetane chemiluminescence substrate CDP-Star™ (Boehringer Mannheim) in 100 mM Tris/HCl, pH 9.0, 100 mM NaCl and 1 mM $MgCl_2$. Fluorescent and chemiluminescent signals were imaged and quantified with

EXAMPLE 9

Microtitre Plate Filter Retardation Assay

To process a large number of proteolytic digestion reactions in parallel, a microtitre plate filter retardation assay was developed. In this assay a 96-well microtitre plate containing a cellulose acetate membrane with a pore size of 0.45 mm (Whatman Polyfiltronics) was used for the retention of polyglutamine-containing protein aggregates.

The following experimental protocol was employed:

First, 15 µl GST fusion protein solution (200 µg/ml GST-HD51DPBio or GST-HD20DPBio in buffer P [20 mM Tris/HCl (pH 8.0), 150 mM NaCl]) and 15 µl trypsin solution (10 µg/ml trypsin (Boehringer Mannheim, sequencing grade) in buffer P) were combined in a 96-well Thermo-Fast®96 tube plate (Advanced Biotechnologies LTD) using a multi channel pipette (Eppendorf), and the microtitre plate was incubated for 16 hours at 37° C. Then 30 µl SDS/DTTsolution (4% SDS, 100 mM DTT in buffer P) were added to each well, the plate was sealed with a microtitre plate sealer (Biostat LTD) and the plate was heated in a 96-well MasterCycler (Eppendorf-Netheler-Hinz) for 5 min at 98° C.

The sealing was removed and 50 µl of the reaction mix were transferred into each well of a new 96-well microtitre plate containing a 0.45 µm cellulose acetate membrane, pre-equilibrated with 0.1% (w/v) SDS, using a multi channel pipette. For equilibration of the cellulose acetate membrane, the microtitre plate was placed into the QIAvac Manifold-96 (Qiagen) and 200 µl 0.1% SDS was pipetted into each well of the plate. Vacuum was then applied until the SDS solution had passed through the filter. Prior to addition of the protein solution, each well of the filter plate was preloaded with an additional 200 µl of 0.1% SDS. The diluted protein solution was then filtered through the membrane by applying vacuum.

The filterplate was washed with 2×200 µl 0.1% SDS and 2×200 ml TBS (100 mM Tris/HCl (pH 7.4), 150 mM NaCl). Vacuum was used to remove wash solutions from the membrane. 200 µl 0.2% (w/v) BSA in TBS were pipetted into each well of the filterplate, and the plate was incubated for 1 h at room temperature (RT) (blocking). Blocking buffer was removed by pipetting.

Next, 200 µl streptavidin alkaline phosphatase (1:1000, Promega) in 0.2% (w/v) BSA/TBS were added to each sample, and the filterplate was incubated for 1 h at RT. Streptavidin AP buffer was removed by pipetting. The filterplate was washed with 3×200 µl TTBS [100 mM Tris/HCl (pH 7.4), 150 mM NaCl, 0.1% (v/v) Tween 20] and 3×200 µl TBS. Vacuum was used to remove wash solutions.

200 µl detection buffer (50 mM Tris/HCl (pH 9.0), 500 mM NaCl, 1 mM Mg $Cl_2$) were added to each sample, incubated for 1 min and vacuum was applied to remove the buffer. 200 µl Attophos™ (10 mM AttoPhos™) in detection buffer were pipetted into each well of the filterplate, incubated for 1 h at RT, vacuum was applied to remove the buffer, and the fluorescence emission of each well was measured with the CytoFluor®4000 (Persptive Biosystems) at 485+/−20 (excitation) and 530+/−25 (emission). Finally, the resultant images were analysed with CytoFluor 4.1 software and MS Excel 7.0.

As expected from the text set of experiments, using fusions of GST and the full-length HD exon 1 protein, only the cleavage products of GST-HD51 DP were retained by the filter and were detected by the huntingtin-specific antibody HD1, indicating the formation of high molecular weight HD51DP aggregates from this fusion protein. Scanning electron microscopy of the material retained on the surface of the membrane revealed bunches of long fibrils or filaments (FIG. 9B), which were not detected after filtration of the uncleaved GST-HD51DP preparation or the protease-treated GST-HD20DP preparation. These results indicate that an elongated polyglutamine sequence but not the proline rich region in the HD exon 1 protein is necessary for the formation of high molecular weight protein aggregates in vitro.

Figure 11:
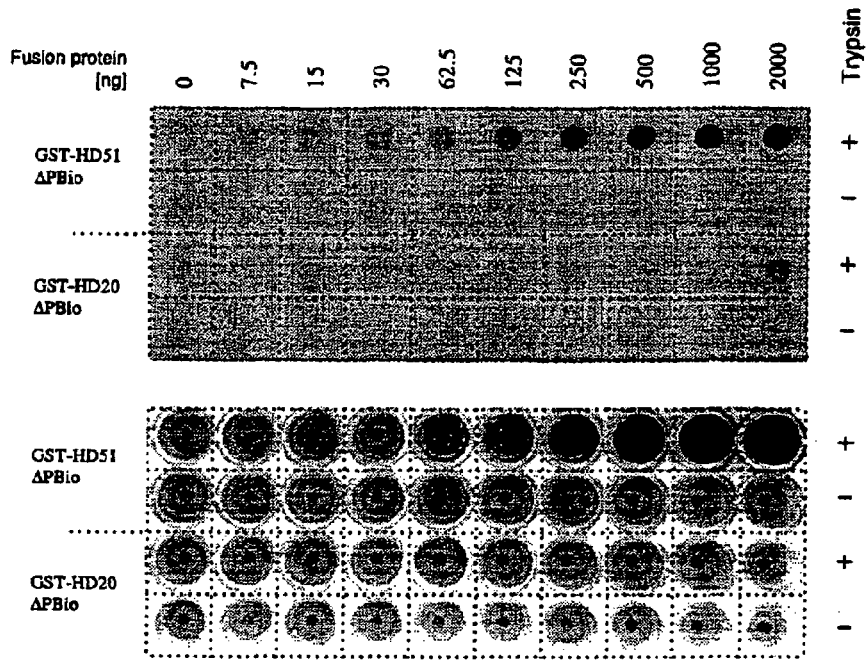
Figure 11:
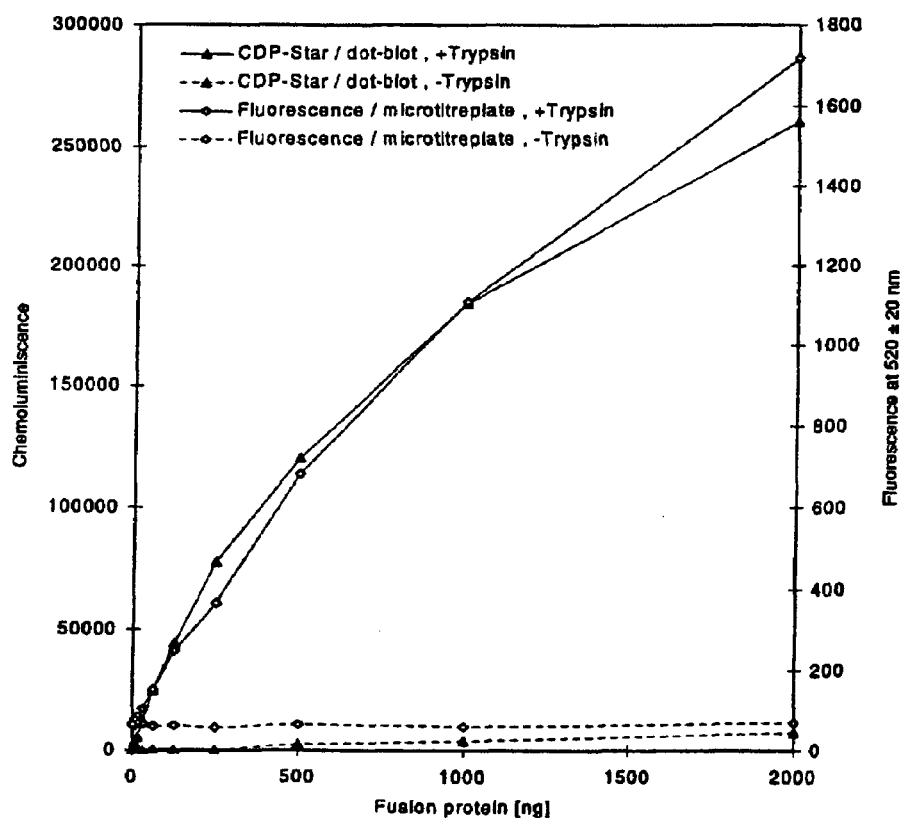

Essentially, the same results as with the dot blot filter retardation assay were obtained when the fusion proteins GST-HD20DPBio and -HD51DPBio were analysed with the microtitre plate filter retardation assay, indicating that this assay can be used for the high throughput isolation of chemical compounds from chemical libraries (FIGS. 11A and 11B).

REFERENCES

Bates, G. P., Mangiarini, L., Mahal, A. and Davies, S. W. (1997). Transgenic models of Huntington's disease. Hum. Mol. Genet. 6, 1633–1637.

Booth, D. R., Stunde, M., Bellotti, V., Robinson, C. V., Hutchinson, W. L., Fraser, P. E., Hawkins, P. N., Dobson, C. M., Radford, S. E., Blake, C. C. F., and Pepys, M. B. (1997). Instability, unfolding and aggregation of human lysozyme variants underlying amyloid fibrillogenesis. Nature 385, 787–793.

Burke, J. R., Enghild, J. J., Martin, M. E., Jou, Y.-S., Myers, R. M., Roses, A. D., Vance, J. M., and Strittmatter, W. J. (1996). Huntingtin and DRPLA proteins selectively interact with the enzyme GAPDH. Nature Med. 2, 347–350.

Caputo, C. B., Fraser, P. E., Sobel, I. E., and Krischner, D. A. (1992). Amyloid-like properties of a synthetic peptide corresponding to the carboxy terminus of b-amyloid protein precursor. Arch. Bioch. Biophys. 292,199–205.

Caughey, B., and Chesebro, B. (1997). Prion protein and the transmissible spongiform encephalopaties. Trends Cell Biol. 7, 56–62.

Davies, S. W., Trumaine, M., Cozens, B. A., DiFiglia, M., Sharp, A. H., Ross, C. A., Scherzinger, E., Wanker, E. E., Mangiarini, L., and Bates, G. P. (1997). Formation of neuronal intranuclear inclusions (NII) underlies the neurological dysfunction in mice transgenic for the HD mutation. Cell 90, 537–548.

de Rooij, K. E., Dorsman, J. C., Smoor, M. A., T., d. D. J., and van Ommen, G.-J. (1996). Subcellular localisation of the Huntington's disease gene product in cell lines by immunofluorescence and biochemical subcellular fractionation. Hum. Mol. Genet 5, 1093–1099.

DiFiglia, M., Sapp, E., Chase, K., Schwarz, C., Meloni, A., Young, C., Martin, E., Vonstattel, J.-P., Carraway, R., Reeves, S. A., Boyce, F. M., and Aronin, N. (1995). Huntingtin is a cytoplasmic protein associated with vesicles in human and rat brain neurons. Neuron 14, 1075–1081.

Duyao, M. P., Auerbach, A. A., Ryan, A., Persichetti, F., Barnes, G. T., McNeil, S. M., Ge, P., Vonstattel, J.-P., Gusella, J. F., Joyner, A. L., and MacDonald, M. E. (1995). Inactivation of the mouse Huntington's disease gene homolog Hdh. Science 269,407–410.

Glenner, G. G. (1980). Amyloid deposits and amyloidosis. N. Engl. J. Med. 302, 1283–1292, 1333–1343.

Goldberg, Y. P., Nicholson, D. W., Rasper, D. M., Kalchman, M. A., Koide, H. B., Graham, R. K., Bromm, M., Kazemi-Esfarjani, P., Thornberry, N. A., Vaillancourt, J. P., and Hayden, M. R. (1996). Cleavage of huntingtin by apopain, a proapoptotic cysteine protease, is modulated by the polyglutamine tract. Nature Genet. 13, 442–449.

Gutekunst, C.-A., Levey, A. I., Heilman, C. J., Whaley, W. L., Yi, H., Nash, N. R., Rees, H. D., Madden, J. J., and Hersch, S. M. (1995). Identification and localization of huntingtin in brain and human lymphoblastoid cell lines with anti-fusion protein antibodies. Proc. Natl. Acad. Sci. USA 92, 8710–8714.

Harper, P. S. (1991). Huntington's disease, 22 Edition, P. S. Harper, ed. (London: W.B. Saunders Co, Ltd).

HDCRG (1993). A novel gene containing a trinucleotide repeat that is unstable on Huntington's disease chromosomes. Cell 72, 971–983.

Hoogeveen, A. T., Willemsen, R., Meyer, N., de Rooij, K. E., Roos, R. A. C., van Ommen, G.-J. B., and Galjaard, H. (1993). Characterisation and localisation of the Huntington disease gene product. Hum. Mol. Genet. 2, 2069–2073.

Ikeda, H., Yamaguchi, M., Sugai, S., Aze, Y., Narumija, S., and Kakizuka, A. (1996). Expanded polyglutamine in the Machado-Joseph disease protein induces cell death in vitro and in vivo. Nature Genet. 13,196–202.

Jarrett, J. T., and Lansburry, P. T. (1993). Seeding "one-dimensional crystallization" of amyloid: a pathogenic mechanism in Alzheimer's disease and scrapie? Cell 73, 1055–1058.

Kalchman, M. A., Graham, R. K., Xia, G., Koide, H. B., Hodgson, J. G., Graham, K. C., Goldberg, Y. P., Gietz, R. D., Pickart, C. M., and Hayden, M. R. (1996). Huntingtin is ubiquinated and interacts with a specific ubiquitin-conjugating enzyme. J. Biol. Chem. 271, 19385–19394.

Kalchman, M. A., Koide, H. B., McCutcheon, K., Graham, R. K., Nichol, K., Nishiyama, K., Kazemi-Esfariani, P., Lynn, F. C., Wellington, C., Metzler, M., Goldberg, Y. P., Kanazawa, I., Gietz, R. D., and Hayden, M. R. (1997). HIP1, a human homologue of S. cerevisiae Sla2p, interacts with mambrane-associated huntingtin in the brain. Nature Genet. 16, 44–53.

Li, X.-J., Li, S.-H., Sharp, A. H., Nucifora, F. C., Schilling, G., Lanahan, A., Worley, P., Snyder, S. H., and Ross, C. A. (1995). A huntingtin-associated protein enriched in brain with implications for pathology. Nature 378, 398–402.

Lim, K., Ho, J. X., Keeling, K., Gilliland, G. L., JI, X., Rüker, F., and Carter, D. C. (1994). Three-dimensional structure of Schistosoma japonicum glutamine S-transferase fused with a six-amino acid conserved neutralizing epitope of gp41 from HIV. Prot. Sci. 3, 2233–2244.

Mangiarini, L., Sathasivam, K., Seller, M., Cozens, B., Harper, A., Hetherington, C., Lawton, M., Trottier, Y., Lehrach, H., Davies, S. W., and Bates, G. P. (1996). Exon 1 of the Huntington's disease gene containing a highly expanded CAG repeat is sufficient to cause a progressive neurological phenotype in transgenic mice. Cell 87, 493–506.

Onodera, O., Roses, A. D., Tsuji, S., Vance, J. M., Stritmatter, W. J., and Burke, J. R. (1996). Toxicity of expanded polyglutamine-domain proteins in Escherichia coli. FEBS Lett. 399, 135–139.

Perutz, M. F. (1996). Gulutamine repeats and inherited neurodegenerative diseases: molecular aspects. Curr. Opin. Struct. Biol. 6, 848–858.

Perutz, M. F., Johnston, T., Suzuki, M., and Finch, J. T. (1994). Glutamine repeats as polar zippers: their possible role in neurodegenerative diseases. Proc. Natl. Acad. Sci. USA 91, 5355–5358.

Portera-Cailliau, C., Hedreen, J. C., Price, D. L., and Koliatsos, V. E. (1995). Evidence of apoptotic cell death in Huntington disease and excitotoxic animal models. J. Neurosci. 15, 3775–3787.

Prusiner, S. B., Kinley, M. P. M., Bowman, K. A., Bolton, D. C., Bendheim, P. E., Groth, D. F., and Glenner, G. G. (1983). Scrapie prions aggregate to form amyloid-like birefingent rods. Cell 35, 349–358.

Roizin, L., Stellar, S., and Liu, J. C. (1979). Neuronal nuclear-cytoplasmic changes in Huntington's Chorea: Electron microcope investigations. Adv. Neurol. 23, 95–122.

Roos, R. A. C., and Bots, G. T. A. M. (1983). Nuclear membrane indentations in Huntington's chorea. J. Neurol. Sci. 61, 37–47.

Ross, C. A. (1995). When more is less: pathogenesis of glutamine repeat neurodegenerative diseases. Neuron 15, 493–496.

Rubinsztein, D. C., Leggo, J., Coles, R., Almqvist, E., Biancalana, V., Cassiman, J.-J., Chotai, K., Connarty, M., Crauford, D., Curtis, A., Curtis, D., Davidson, M. J., Differ, A.-M., Dode, C., Dodge, A., Frontali, M., Ranen, N. G., Stine, O. C., Sherr, M., Abbott, M. H., Franz, M. L., Graham, C. A., Harper, P. S., Hedreen, J. C., Jackson, A., Kaplan, J.-C., Losekoot, M., MacMillan, J. C., Morrison, P., Trottier, Y., Novelletto, A., Simpson, S. A., Theilmann, J., Whittaker, J. L., Folstein, S. E., Ross, C. A., and Hayden, M. R. (1996). Phenotypic characterisation of individuals with 30–40 CAG repeats in the Huntington's disease (HD) gene reveals HD cases with 36 repeats and apparently normal elderly individuals with 36–39 repeats. Am. J. Hum. Genet. 59, 16–22.

Sathasivam, K., Amaechi, I., Mangiarini, L., and Bates, G. P. (1997). Identification of an HD patient with a (CAG) 180 repeat expansion and the propagation of highly expanded CAG repeats in lambda phage. Hum Genet. 99, 692–695.

Sharp, A. H., Loev, S. J., Schilling, G., Li, S.-H., Li, X.-J., Bao, J., Wagster, M. V., Kotzuk, J. A., Steiner, J. P., Lo, A., Hedreen, J., Sisodia, S., Snyder, S. H., Dawson, T. M., Ryugo, D. K., and Ross, C. A. (1995). Widespread expression of Huntington's disease gene (IT15) protein product. Neuron 14, 1065–1074.

Smith, D. B., and Johnson, K. S. (1988). Single-step purification of peptides expressed in Escherichia coli as fusions with glutathione S-transferase. Gene 67, 31–40.

Stott, K., Blackburn, J. M., Butler, P. J. G., and Perutz, M. (1995). Incorporation of glutamine repeats makes protein oligomerize: implications for neurodegenerative diseases. Proc. Natl. Acad. Sci. USA 92, 6509–6513.

Tellez-Nagel, I., Johnson, B., and Terry, R. D. (1974). Studies on brain biopsies of patients with Huntington's chorea. J. Neurocyt. 3, 308–332.

Towbin, H., Staehelin, T., and Gordon, J. (1979). Electrophoretic transfer of proteins from polyacrylamide gels to nitrocellulose sheets: procedure and some applications. Proc. Natl. Acad. Sci. USA 76, 4350–4354.

Trottier, Y., Devys, D., Imbert, G., Sandou, F., An, i., Lutz, Y., Weber, C., Agid, Y., Hirsch, E. C., and Mandel, J.-L. (1995a). Cellular localisation of the Huntington's disease protein and discrimination of the normal and mutated forms. Nature Genet. 10, 104–110.

Trottier, Y., Lutz, Y., Stevanin, G., Imbert, G., Devys, D., Cancel, G., Sandou, F., Weber, C., David, G., Tora, L., Agid, Y., Brice, A., and Mandel, J.-L. (1995b). Polyglutamine expansion as a pathological epitope in Huntington's disease and four dominant cerebellar ataxias. Nature 378, 403–406.

Vonsattel, J.-P., Myers, R. H., Stevens, T. J., Ferrante, R. J., Bird, E. D., and Richardson, E. P. (1985). Neuropathological classification of Huntington's disease. J. Neuropath. Exp. Neurol. 44, 559–577.

Wanker, E. E., Rovira, C., Scherzinger, E., Hasenbank, R., Walter, S., Tait, D., Colicelli, J., and Lehrach, H. (1997). HIP-1: A huntingtin interacting protein isolated by the yeast two-hybrid system. Hum. Mol. Genet. 6, 487–495.

M. DiFiglia, E. Sapp, K. O. Chase, S. W. Davies, G. P. Bates, J. P. Vonsattel, and N. Aronin, Science 277, 1990 (1997).

M. W. Becher, J. A. Kotzuk, A. H. Sharp, S. W. Davies, G. P. Bates, D. L. Price, and C. A. Ross, Neurobiol. Disease 4, 1 (1997).

S. Igarashi, R. Koide, T. Shimohata, M. Yamada, Y. Hayashi, H. Takano, H. Date, M. Oayke, T. Sato, A. Sato, S. Egawa, T. Ikeuchi, H. Tanaka, R. Nakano, K. Tanaka, I. Hozumi, T. Inuzuka, H. Takahashi, and S. Tsuji, Nature Genetics 18, 11 (1998).

P. J. Skinner, B. T. Koshy, C. J. Cummings, I. A. Klement, K. Helin, A. Servadio, H. Y. Zoghbi, and H. T. Orr, Nature 389, 971 (1997).

A. Matilla, B. T. Koshy, C. J. Cummings, T. Isobe, H. T. Orr, and H. Y. Zoghbi, Nature 389, 974 (1997).

H. L. Paulson, M. K. Perez, Y. Trottier, J. Q. Trojanowski, S. H. Subramony, S. S. Das, P. Vig, J.-I. Mandel, K. H. Fischbeck, and R. N. Pittman, Neuron 19, 333 (1997).

M. Holmberg, C. Duyckaerts, A. Durr, G. Cancel, I. Gourfinkel-An, P. Damier, B. Faucheux, Y. Trottier, E. C. Hirsch, Y. Agid, and A. Brice, Hum. Mol. Genet. 7, 913 (1998).

We claim:

1. A composition comprising
   (a) a nucleic acid molecule encoding a fusion protein comprising
      (aa) a glutathione S-transferase (GST) (poly)peptide that enhances solubility and/or prevents aggregation of said fusion protein; and
      (ab) a huntingtin (poly)peptide that has the ability to self-assemble into fibrils or protein aggregates, wherein connection of polypeptides (aa) and (ab) is via a linker or by a direct attachment, and wherein at least one of the linker, (poly)peptide (aa) and (poly)peptide (ab) includes a cleavable site, and wherein said huntingtin (poly)peptide self-assembles subsequent to release from said fusion protein,
   (b) a vector containing the nucleic acid molecule of (a);
   (c) a host transformed with the vector of (b); and/or
   (d) a fusion protein encoded by the nucleic acid of (a).

2. The composition of claim 1 wherein the huntingtin (poly)peptide comprises a polyglutamine expansion.

3. The composition of claim 2 wherein said polyglutamine expansion comprises at least 35 glutamines.

4. The composition of claim 3 wherein said polyglutamine expansion comprises at least 51 glutamines.

5. The composition of claim 1 wherein said nucleic acid is DNA.

6. The composition of claim 1 wherein said vector is an expression vector or a gene targeting vector.

7. The composition of claim 1 wherein said host is a bacterial cell, an animal cell, an insect cell, a plant cell, a fungal cell, or a *Pichia pastoris* cell.

8. The composition of claim 7 wherein the bacterial cell is an *E. coli* cell.

9. The composition of claim 7, wherein the animal cell is a mammalian cell.

10. The composition of claim 7, wherein the fungal cell is a yeast cell.

11. The composition of claim 10, wherein the yeast cell is a *Saccharomyces* or *Aspergillus* cell.

12. The composition of claim 1, wherein the huntingtin (poly)peptide consists of a huntingtin (poly)peptide encoded by the nucleic acid sequence of huntingtin exon 1 and includes a polyglutamine expansion that comprises at least 35 glutamines.

13. The composition of claim 12, wherein the polyglutamine expansion comprises at least 51 glutamines.

* * * * *